(12) United States Patent
Chapman et al.

(10) Patent No.: US 12,350,505 B2
(45) Date of Patent: Jul. 8, 2025

(54) DEFIBRILLATORS WITH ENHANCED FUNCTIONALITY DURING CARDIOPULMONARY RESUSCITATION PERIODS

(71) Applicant: Stryker Corporation, Kalamazoo, MI (US)

(72) Inventors: Fred W. Chapman, Newcastle, WA (US); Ryan William Apperson, Bothell, WA (US); Dale R. Beuning, Seattle, WA (US); Steven Barry Duke, Bothell, WA (US); Thangeswaran Natarajan, Bothell, WA (US); Daniel W Piraino, Seattle, WA (US); Mark Rutzer, Seattle, WA (US); David B. Stewart, Carnation, WA (US); Tyson G. Taylor, Bothell, WA (US)

(73) Assignee: Stryker Corporation, Portage, MI (US)

( * ) Notice: Subject to any disclaimer, the term of this patent is extended or adjusted under 35 U.S.C. 154(b) by 481 days.

(21) Appl. No.: 17/559,925

(22) Filed: Dec. 22, 2021

(65) Prior Publication Data
US 2022/0193431 A1 Jun. 23, 2022

Related U.S. Application Data

(60) Provisional application No. 63/130,167, filed on Dec. 23, 2020.

(51) Int. Cl.
*A61N 1/39* (2006.01)
(52) U.S. Cl.
CPC ....... *A61N 1/39044* (2017.08); *A61N 1/3925* (2013.01)

(58) Field of Classification Search
CPC .................. A61N 1/39044; A61N 1/3925
See application file for complete search history.

(56) References Cited

U.S. PATENT DOCUMENTS

| 5,687,735 | A | 11/1997 | Forbes et al. |
| 5,853,364 | A | 12/1998 | Baker, Jr. et al. |

(Continued)

FOREIGN PATENT DOCUMENTS

| EP | 2968965 B1 | 1/2016 |
| EP | 2295111 B1 | 7/2017 |

(Continued)

OTHER PUBLICATIONS

Aramendi, et al., "A Simple Effective Filtering Method for Removing CPR Caused Artefacts from Surface ECG Signals," Computers in Cardiology, Sep. 2005, pp. 547-550.

(Continued)

*Primary Examiner* — Joseph M Dietrich
(74) *Attorney, Agent, or Firm* — Lee & Hayes, P.C.

(57) ABSTRACT

Defibrillators with enhanced functionality during cardiopulmonary resuscitation (CPR) periods are described. The enhancements include predicting a length of a charging period of a capacitor of the medical device so that capacitor is shock charged at the end of the CPR period. The enhancements also include re-assessing an electrocardiogram (ECG) signal for continued presence of a shockable rhythm during the CPR period and before administration of a defibrillation shock. Together the enhancements can improve the timing and recommended administration of defibrillation therapy.

20 Claims, 9 Drawing Sheets

(56) References Cited

U.S. PATENT DOCUMENTS

| | | | |
|---|---|---|---|
| 6,334,070 | B1 | 12/2001 | Nova et al. |
| 6,356,785 | B1 | 3/2002 | Snyder et al. |
| 6,752,771 | B2 | 6/2004 | Rothman et al. |
| 7,039,457 | B2 | 5/2006 | Young et al. |
| 7,220,235 | B2 | 5/2007 | Geheb et al. |
| 7,369,345 | B1 | 5/2008 | Li et al. |
| 7,565,194 | B2 | 7/2009 | Tan et al. |
| 7,567,837 | B2 | 7/2009 | Weil et al. |
| 7,650,181 | B2 | 1/2010 | Freeman et al. |
| 7,831,299 | B2 | 11/2010 | Tan et al. |
| 7,904,152 | B2 | 3/2011 | Sullivan et al. |
| 8,903,498 | B2 | 12/2014 | Sullivan et al. |
| 9,084,545 | B2 | 7/2015 | Sullivan et al. |
| 9,180,304 | B2 | 11/2015 | Quan et al. |
| 9,186,521 | B2 | 11/2015 | Quan et al. |
| 9,204,845 | B2 | 12/2015 | Sullivan et al. |
| 9,545,211 | B2 | 1/2017 | Sullivan et al. |
| 9,642,575 | B2 | 5/2017 | Freeman et al. |
| 9,751,534 | B2 | 9/2017 | Fung et al. |
| 9,801,561 | B2 | 10/2017 | Sullivan et al. |
| 9,919,160 | B2 | 3/2018 | Firoozabadi et al. |
| 10,080,904 | B2 | 9/2018 | Sullivan |
| 10,117,804 | B2 | 11/2018 | Nilsson et al. |
| 10,155,120 | B2 | 12/2018 | Zaidi et al. |
| 10,258,248 | B2 | 4/2019 | Quan et al. |
| 10,905,344 | B2 | 2/2021 | Sullivan et al. |
| 2002/0165471 | A1 | 11/2002 | Halperin et al. |
| 2005/0101889 | A1 | 5/2005 | Freeman et al. |
| 2005/0137628 | A1 | 6/2005 | Young et al. |
| 2005/0256415 | A1 | 11/2005 | Tan et al. |
| 2006/0025824 | A1 | 2/2006 | Freeman et al. |
| 2006/0149157 | A1 | 7/2006 | Weil et al. |
| 2006/0235320 | A1 | 10/2006 | Tan et al. |
| 2006/0258927 | A1 | 11/2006 | Edgar et al. |
| 2007/0100379 | A1 | 5/2007 | Tan et al. |
| 2007/0142735 | A1 | 6/2007 | Shin et al. |
| 2007/0162076 | A1 | 7/2007 | Tan et al. |
| 2009/0204162 | A1 | 8/2009 | Addison et al. |
| 2010/0016685 | A1 | 1/2010 | Muehlsteff et al. |
| 2010/0076510 | A1 | 3/2010 | Lyster |
| 2011/0034816 | A1 | 2/2011 | Tan et al. |
| 2011/0082510 | A1 | 4/2011 | Sullivan |
| 2011/0105930 | A1 | 5/2011 | Thiagarajan et al. |
| 2011/0144707 | A1 | 6/2011 | Sullivan et al. |
| 2011/0202100 | A1 | 8/2011 | Tan et al. |
| 2011/0202101 | A1 | 8/2011 | Tan et al. |
| 2012/0010543 | A1 | 1/2012 | Johnson et al. |
| 2012/0016279 | A1 | 1/2012 | Banville et al. |
| 2012/0157865 | A1 | 6/2012 | Stein et al. |
| 2013/0184600 | A1 | 7/2013 | Tan et al. |
| 2014/0088374 | A1 | 3/2014 | Sullivan et al. |
| 2014/0100497 | A1 | 4/2014 | Hayashi et al. |
| 2014/0243915 | A1 | 8/2014 | Freeman et al. |
| 2015/0297107 | A1 | 10/2015 | Sullivan et al. |
| 2015/0352367 | A1 | 12/2015 | Quan et al. |
| 2016/0008613 | A1 | 1/2016 | Snyder |
| 2016/0220833 | A1* | 8/2016 | Tan .................... A61B 5/11 |
| 2017/0105644 | A1 | 4/2017 | Sullivan et al. |
| 2017/0361120 | A1 | 12/2017 | Liu et al. |
| 2018/0303367 | A1 | 10/2018 | Sullivan et al. |
| 2019/0059745 | A1 | 2/2019 | Tan et al. |
| 2019/0374428 | A1 | 12/2019 | Kaufman et al. |
| 2020/0253495 | A1 | 8/2020 | Tan et al. |
| 2021/0015387 | A1 | 1/2021 | Sullivan et al. |
| 2021/0030294 | A9 | 2/2021 | Sullivan et al. |
| 2022/0193429 | A1 | 6/2022 | Chapman et al. |
| 2022/0193430 | A1 | 6/2022 | Chapman et al. |
| 2022/0193433 | A1 | 6/2022 | Chapman et al. |

FOREIGN PATENT DOCUMENTS

| | | | |
|---|---|---|---|
| JP | 4890687 B2 | 3/2012 | |
| JP | 6090776 B2 | 3/2017 | |
| WO | WO2009071128 A1 | 6/2009 | |

OTHER PUBLICATIONS

Aramendi, et al., "Detection of ventricular fibrillation in the presence of cardiopulmonary resuscitation artefacts," Resuscitation (2007) 72, Jan. 2007, pp. 115-123.

Aramendi, et al., "Suppression of the cardiopulmonary resuscitation artefacts using the instantaneous chest compression rate extracted from the thoracic impedance," Resuscitation 83 (2012), Jun. 2012, pp. 692-698.

Berger, et al., "Rhythm discrimination during uninterrupted CPR using motion artifact reduction system," Resuscitation (2007) 75, Oct. 2007, pp. 145-152.

Dotsinsky, et al., "Fast Electrocardiogram Amplifier Recovery after Defibrillation Shock," Bioautomation (2005) 2, Apr. 2005, pp. 76-84.

Dotsinsky, "Suppression of AC railway power-line interference in ECG signals recorded by public access defibrillators," BioMedical Engineering OnLine (2005) 4:65, Nov. 2005, 8 pages.

Extended European Search Report, mailed Mar. 1, 2017, EP Application No. 16178129.9, filed Jul. 6, 2016, 17 pages.

Granegger, et al., "Use of independent component analysis for reducing CPR artefacts in human emergency ECGs," Resuscitation (2011) 82(1), Jan. 2011, pp. 79-84.

Irusta, et al., "A Least Mean Square Filter for the Estimation of the Cardiopulmonary Resuscitation Artifact Based on the Frequency of the Compressions," IEEE Transaction on Biomedical Engineering (2009) 56:(4), Apr. 2009, pp. 1052-1062.

International Search Report and Written Opinion for PCT/US13/39555, mailed on Oct. 1, 2013, 22 pages.

Lee, et al., "Adaptive Comb Filtering for Motion Artifact Reduction from PPG with a Structure of Adaptive Lattice IIR Notch Filter," 33rd Annual International Conference of the IEEE EMBS, Boston, MA, Aug. 30-Sep. 3, 2011, pp. 7937-7940.

Office Action for U.S. Appl. No. 14/656,666, mailed on Jan. 25, 2016, Sullivan, "System and Method for Electrocardiogram Analysis and Optimization of Cardiopulmonary Resuscitation and Therapy Delivery," 11 pages.

Office Action for U.S. Appl. No. 13/836,062, mailed on Jan. 31, 2014, Sullivan, "System and Method for Electrocardiogram Analysis and Optimization of Cardiopulmonary Resuscitation and Therapy Delivery", 4 pages.

Office Action for U.S. Appl. No. 13/676,593, mailed on Nov. 26, 2014, Sullivan, "Filter Mechanism for Removing ECG Artifact From Mechanical Chest Compressions", 6 pages.

Office Action for U.S. Appl. No. 15/796,575, mailed on Dec. 26, 2019, Sullivan, "System and Method for Electrocardiogram Analysis and Optimization of Cardiopulmonary Resuscitation and Therapy Delivery", 7 pages.

Office Action for U.S. Appl. No. 13/676,593, mailed on Feb. 7, 2014, Sullivan, "Filter Mechanism for Removing ECG Artifact From Mechanical Chest Compressions", 12 pages.

Office Action for U.S. Appl. No. 15/395,780, mailed on Mar. 8, 2017, Sullivan, "System and Method for Electrocardiogram Analysis and Optimization of Cardiopulmonary Resuscitation and Therapy Delivery," 6 pages.

Office Action for U.S. Appl. No. 15/796,575, mailed on Apr. 1, 2019, Sullivan, "System and Method for Electrocardiogram Analysis and Optimization of Cardiopulmonary Resuscitation and Therapy Delivery", 7 pages.

Office Action for U.S. Appl. No. 14/558,610, mailed on May 12, 2015, Sullivan, "System and Method for Electrocardiogram Analysis and Optimization of Cardiopulmonary Resuscitation and Therapy Delivery", 10 pages.

Office Action for U.S. Appl. No. 14/656,666, mailed on May 25, 2016, Sullivan, "System and Method for Electrocardiogram Analysis and Optimization of Cardiopulmonary Resuscitation and Therapy Delivery," 9 pages.

Office Action for U.S. Appl. No. 13/676,593, mailed on Jun. 11, 2014, Sullivan, "Filter Mechanism for Removing ECG Artifact From Mechanical Chest Compressions", 10 pages.

(56) References Cited

OTHER PUBLICATIONS

Office Action for U.S. Appl. No. 15/796,575, mailed on Aug. 29, 2019, Sullivan, "System and Method for Electrocardiogram Analysis and Optimization of Cardiopulmonary Resuscitation and Therapy Delivery", 6 pages.

Ruiz de Gauna, et al., "A method to remove CPR artefacts from human ECG using only the recorded ECG," Resuscitation (2008) 76(2), Feb. 2008, pp. 271-278.

Ruiz, et al., "Cardiopulmonary resuscitation artefact suppression using a Kalman filter and the frequency of chest compressions as the reference signal," Resuscitation (2010) 81(9), Sep. 2010, pp. 1087-1094.

Office Action issued for U.S. Appl. No. 17/559,795 on Mar. 28, 2024.

Office Action issued for U.S. Appl. No. 17/559,992 on May 2, 2024.

Office Action for U.S. Appl. No. 17/560,043, mailed on Jul. 3, 2024, Chapman, "Enhanced Defibrillation Shock Decisions", 28 Pages.

Office Action for US patent Application Aug. 30, 2024, mailed on Aug. 30, 2024, Chapman, "Up-to-Date Defibrillation Recommendations Based on Continuous ECG Analysis During Cardiopulmonary Resuscitation",4 pgs.

Porciuncula, et al., "Wearable Movement Sensors for Rehabilitation: A Focused Review of Technological and Clinical Advances", HHS Public Access, PM R. Sep. 2018; 10(9 Suppl 2):S220-S232. doi: 10.1016/j.pmrj.2018.06.013, 2019, 21 pgs.

Office Action for U.S. Appl. No. 17/560,043, dated Jan. 31, 2025, Chapman, "Enhanced Defibrillation Shock Decisions", 31 pages.

Office Action for U.S. Appl. No. 17/559,795, dated Dec. 11, 2024, Chapman, "Detecting and Addressing Irregular Motion to Improve Defibrillation Shock Recommendations", 33 Pages.

* cited by examiner

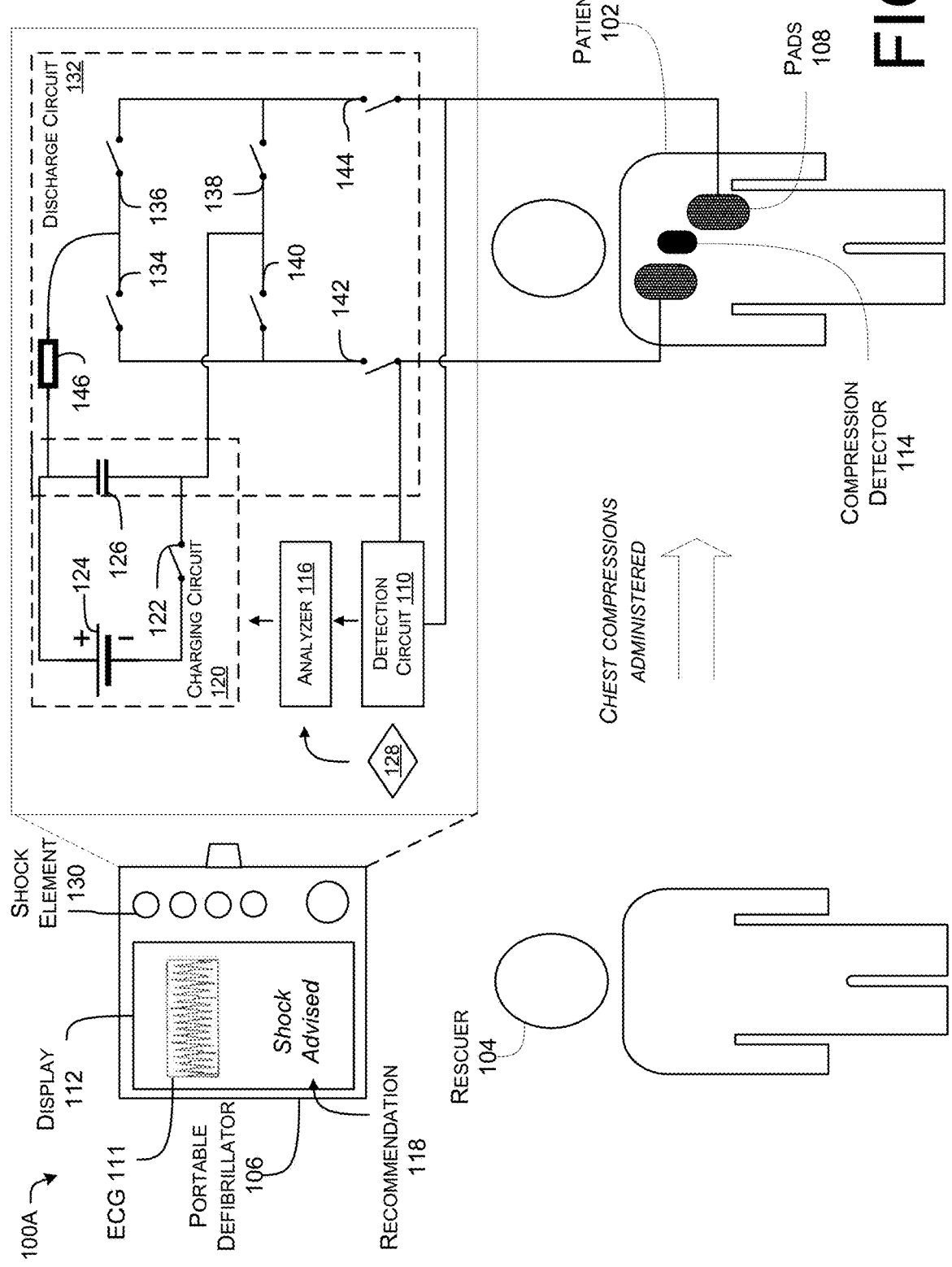

DEFIBRILLATORS WITH ENHANCED FUNCTIONALITY DURING CARDIOPULMONARY RESUSCITATION PERIODS

CROSS-REFERENCE TO RELATED APPLICATION

This application claims the priority of U.S. Provisional Application No. 63/130,167, titled "DEFIBRILLATORS WITH ENHANCED FUNCTIONALITY DURING CARDIOPULMONARY RESUSCITATION PERIODS," which was filed on Dec. 23, 2020 and is incorporated by reference herein in its entirety.

BACKGROUND

Cardiac arrest is a condition in which an individual's heart ceases to function effectively. During cardiac arrest, the brain and other vital organs are unable to receive sufficient oxygenated blood, which can result in a sudden loss of consciousness. If untreated shortly after onset, cardiac arrest can result in long-term deficits or death. Thus, effective treatments must be applicable in a variety of environments where cardiac arrest is likely to occur, such as environments outside of hospitals or other specialized facilities for administering medical care.

Cardiopulmonary resuscitation (CPR) is a treatment that forces blood to vital organs using chest compressions, which can be administered manually or via a chest compression device, such as the LUCAS 3®, by Stryker Corporation of Kalamazoo, Michigan. CPR is indicated for individuals experiencing cardiac arrest and can slow down damage to the vital organs by providing at least some blood flow despite the heart's disfunction. However, the underlying cause of the cardiac arrest is not treatable by CPR.

Some forms of cardiac arrest are the result of abnormal heart rhythms, such as ventricular fibrillation (VF) and pulseless ventricular tachycardia (V-tach). VF and pulseless V-tach are treatable by defibrillation, which is the delivery of an electrical shock to the heart. Because a defibrillation shock can be dangerous if administered to individuals without VF or pulseless V-tach, a medical device will generally identify and/or assist in the diagnosis of VF and pulseless V-tach based on electrocardiograms (ECGs). An ECG includes one or more lead signals that are indicative of the electrical activity of an individual's heart over time.

BRIEF DESCRIPTION OF THE DRAWINGS

FIGS. 1A to 1C illustrate examples of an emergency environment over time. FIG. 1A illustrates an example of the emergency environment at a first time. FIG. 1B illustrates an example of the emergency environment at a second time. FIG. 1C illustrates an example of the emergency environment at a third time.

DETAILED DESCRIPTION

Figure 1B:
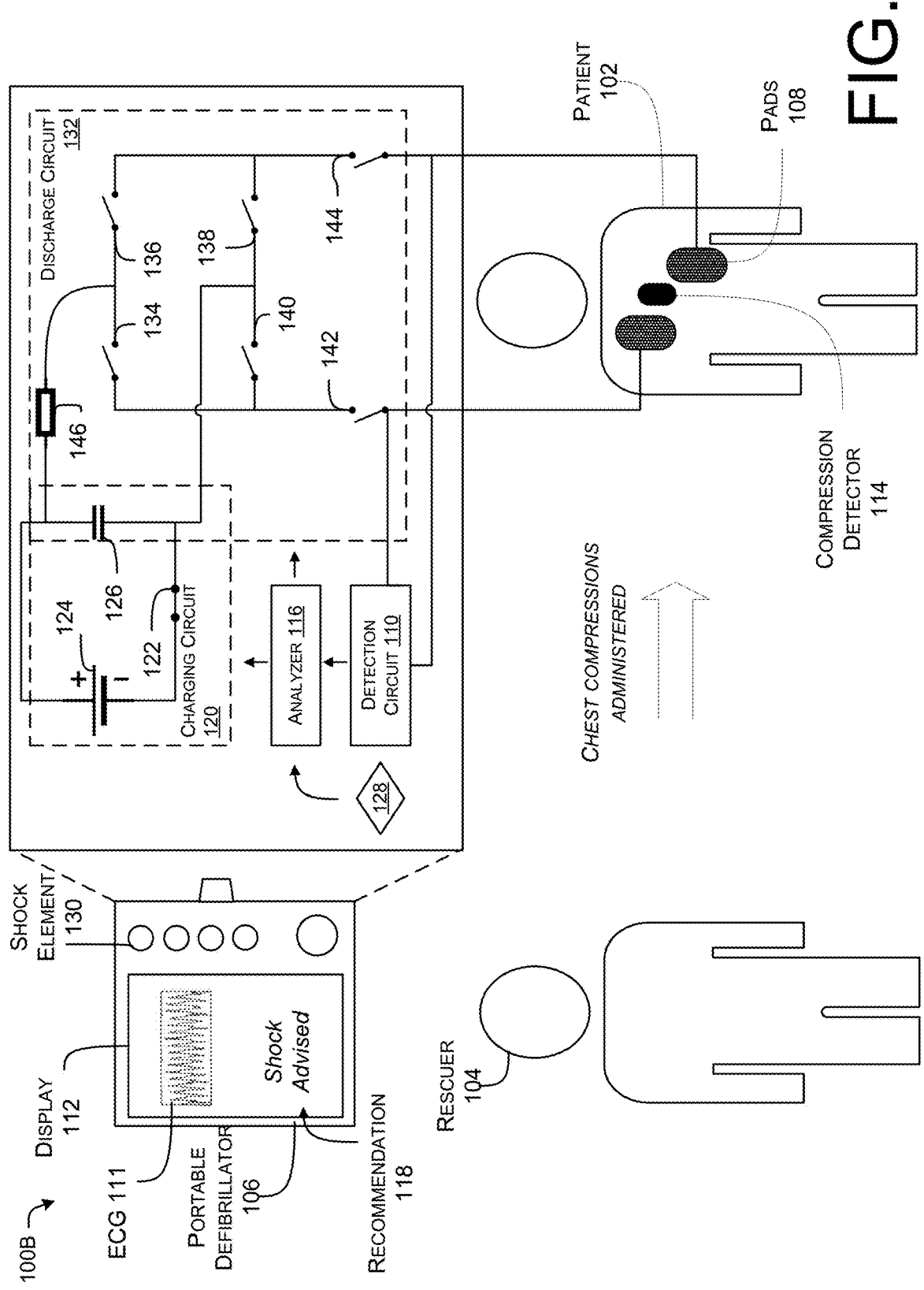

Various implementations described herein relate to systems, devices, and methods for filtering and analyzing of an ECG containing a chest compression artifact based on a predicted charging time (also referred to as a "charging period") of a defibrillator. For instance, various medical devices described herein determine whether an individual has a shockable rhythm and fully charge a capacitor in accordance with a desired defibrillation shock dosage level by the time a CPR period has ended. Accordingly, a defibrillation shock can be administered by discharging the capacitor immediately after an appropriate amount of chest compressions are administered, without a significant time delay between the end of the CPR period and the administration of the defibrillation shock.

Various implementations described herein relate to systems, devices, and methods for performing ECG filtering multiple times. For example, a medical device evaluates a first segment of an ECG containing a chest compression artifact and begins charging a capacitor based on determining that the first segment of the ECG exhibits a shockable rhythm. The medical device also evaluates a second segment of the ECG containing a chest compression artifact, and determines whether to administer a defibrillation shock by discharging the capacitor based on the determining whether the second segment of the ECG exhibits the shockable rhythm. Thus, the defibrillation shock is only administered if the portion of the ECG obtained when or shortly before the capacitor is charged indicates that the shockable rhythm is present.

Implementations described herein solve specific problems in the technical field of medical devices. An example portable defibrillator is powered by a battery or other form of long-term energy storage. To administer a defibrillation shock to an individual, the portable defibrillator outputs a significant amount of electrical energy (e.g., 200 J or above) in a short amount of time (e.g., less than a second). However, the battery is incapable of directly outputting such a high amount of electrical energy in the short amount of time. Thus, in various examples, the portable defibrillator uses the battery to charge a capacitor or other form of short-term energy storage and administers the defibrillation shock by discharging the charged capacitor. Unlike the battery, the charged capacitor is capable of outputting the significant amount of electrical energy in the short amount of time. But the capacitor is also more prone to energy dissipation than the battery, which means that unless the capacitor is discharged shortly after being charged, the defibrillation shock administered by the capacitor may be underpowered.

In practice, the example portable defibrillator begins charging the capacitor when the defibrillator determines that a shockable rhythm is present in the individual's ECG, or in response to receiving an input signal from a user that has identified the shockable rhythm in the individual's ECG. In various examples, there is a significant delay between the time at which the battery begins charging the capacitor and the time at which the capacitor is charged and ready to discharge the defibrillation shock. For instance, the charging time of the capacitor takes seconds, tens of seconds, or even longer depending on characteristics of the battery, the capacitor, and other conditions of the portable defibrillator. In examples wherein the shockable rhythm prevents the individual's brain and other vital organs from receiving sufficient oxygen, the delay from charging the capacitor can be significantly detrimental to the individual's long-term health outcomes.

In some examples, the administration of the defibrillation shock is further delayed by the evaluation of the individual's ECG. When the ECG is obtained during a CPR period in which chest compressions are administered to the individual, a significant artifact associated with the chest compressions may make it difficult for the portable defibrillator and/or the user to discern the shockable rhythm in the ECG. In some cases, the portable defibrillator and/or the user wait until the CPR period ends or pauses in order to evaluate whether the shockable rhythm is present in the ECG. Thus, in these cases, the portable defibrillator only begins charging the capacitor after CPR has ended and the portable defibrillator and/or the user determines that the shockable rhythm is present in the ECG. When CPR is paused and the individual is in cardiac arrest, the individual's brain and other vital organs may receive insufficient oxygen and can therefore be susceptible to long-term damage.

Various implementations described herein address these and other problems by determining a time to begin ECG analysis based on a charging period of the capacitor. The portable defibrillator, for instance, predicts the charging period of the capacitor based on one or more factors including characteristics of the battery, characteristics of the capacitor, input from a user, characteristic of the individual being treated, or any combination thereof. The portable defibrillator also predicts an end time of a CPR period, wherein the chest compressions are administered to the individual. In some examples, the portable defibrillator is configured to determine whether the shockable rhythm is present in an ECG segment, which is obtained during the CPR period, by removing a chest compression artifact from the segment and evaluating the segment. The portable defibrillator predicts the analysis period of the ECG segment, which corresponds to the time that the portable defibrillator takes to determine whether the shockable rhythm is present.

According to some examples, the portable defibrillator determines a start time for the analysis period based on the charging period, the end time of the CPR period, and/or the analysis period, such that the portable defibrillator is able to determine that the shockable rhythm is present and to charge the capacitor by the end time of the CPR period. Thus, the charged capacitor is configured to administer the defibrillation shock immediately after the CPR period ends. Implementations described herein shorten a time period between the end time of the CPR period and the time that the defibrillation shock is administered, thereby reducing the long-term impacts of cardiac arrest on the individual.

Other problems associated with the technical field of defibrillation can be addressed by some implementations described herein. In some cases, the heart rhythm of the individual changes during the delay associated with the charging period. For instance, the individual initially exhibits the shockable rhythm, such that the portable defibrillator and/or the user begins to charge the capacitor. However, when the capacitor is charged, the individual no longer exhibits the shockable rhythm. Unless the heart rhythm of the individual is reevaluated, the portable defibrillator and/or the user may cause the charged capacitor to administer the defibrillation shock when the individual is not exhibiting a heart rhythm that can be treated by defibrillation. The unnecessary defibrillation shock can harm the individual, for example by putting the heart into ventricular fibrillation, without significant benefit.

In various implementations of the present disclosure, the heart rhythm of the individual is reevaluated to confirm whether the shockable rhythm persists after the capacitor begins charging. For example, the portable defibrillator determines whether a shockable rhythm is present in a first ECG segment obtained during a first time period. Upon determining that the shockable rhythm is present in the first ECG segment, the portable defibrillator begins charging the capacitor. In addition, the portable defibrillator determines whether the shockable rhythm is present in a second ECG segment obtained during a second time period, which occurs at least partially after the first time period. The portable defibrillator determines whether to administer the defibrillation shock from the charged capacitor based on whether the shockable rhythm is present in the second ECG segment. In some examples, the portable defibrillator refrains from (or advises against) administering the defibrillation shock from the charged capacitor if the shockable rhythm is no longer present in the second ECG segment. However, if the portable defibrillator confirms that the shockable rhythm remains present in the second ECG segment, the portable defibrillator administers (or recommends administration of) the defibrillation shock. Thus, the portable defibrillator is prevented from defibrillating the individual when the individual is unlikely to benefit from defibrillation.

Particular examples will now be described with reference to the accompanying figures. The scope of this disclosure includes individual examples described herein as well as any combination of the examples, unless otherwise specified.

FIGS. 1A to 10 illustrate examples of an emergency environment over time. FIG. 1A illustrates an example of an emergency environment at a first time 100a. The emergency environment 100a includes a patient 102 that is in cardiac arrest and being treated by a rescuer 104 using a portable defibrillator 106. The emergency environment 100A, for example, is remote from a specialized healthcare environment, such as a hospital. The portable defibrillator 106, for instance, is a monitor-defibrillator, an automated external defibrillator (AED), or a combination thereof. The portable defibrillator 106 is an external defibrillator.

The portable defibrillator 106 includes pads 108 that are in contact with the chest of the patient 102. The rescuer 104, for example, connects pads 108 to the chest of the patient 102. The pads 108 are in contact with the skin of the patient 102, according to various implementations. For instance, each of the pads 108 is attached to the skin of the patient 104 by an adhesive and/or a flexible substrate attached to the patient. Although only two pads 108 are illustrated in FIGS. 1A to 10, some examples include more than two pads 108 connected to the patient 102. The pads 108 are connected to the portable defibrillator 106 by wired connections, in some examples.

The portable defibrillator 106 includes a detection circuit 110 that detects electrical signals received by electrodes in the pads 108. For example, the pads 108 includes two or more detection electrodes in contact with the patient 102. In some examples, the detection circuit 110 detects an ECG 111 of the patient 102 based on relative voltages between the detection electrodes. In some instances, the detection circuit 110 detects an impedance of the patient 102 based on a quotient of a voltage/current applied between the detection electrodes and a current/voltage received by the detection electrodes. In some implementations, the detection circuit 110 includes an analog to digital converter than converts the analog form of the ECG 111 and impedance signals into digital data representing a digital form of the ECG 111. The ECG 111 and/or the impedance detected by the detection circuit 110 is displayed on a display 112 of the portable defibrillator 106.

Chest compressions are administered to the patient 102 during a CPR period, which includes the first time at which FIG. 1A portrays. For instance, the chest compressions are administered by the rescuer 104, by another individual, or by a mechanical chest compression device. A compression detector 114 is disposed on the chest of the patient 102. The compression detector 114 includes one or more sensors, such as at least one accelerometer, at least one gyroscope, at least one pressure sensor, or a combination thereof. The sensor(s) of the compression detector 114 detects the chest compressions administered to the patient 102. In some cases, the compression detector 114 provides a signal indicative of the chest compressions to the portable defibrillator 106. For instance, the compression detector 114 includes a transmitter that transmits the signal over a wired and/or wireless connection between the portable defibrillator 106 and the compression detector 114. In some examples, the detection circuit 110 detects the chest compressions based on the impedance of the patient 102, which varies over time based on the chest compressions administered to the patient 102. According to some cases, the mechanical chest compression device transmits a signal indicative of the chest compressions to the portable defibrillator 106 over a wired and/or wireless connection.

The chest compressions cause the ECG 111 detected by the detection circuit 110 to include a compression artifact. For instance, the chest compressions move the pads 108 relative to the patient 102, change the electrical impedance of the patient 102 measured between the detection electrodes, or generate other sources of artifacts and/or noise within the ECG 111. Accordingly, the ECG 111 displayed to the rescuer 102 is artifacted and difficult to analyze.

The detection circuit 110 provides the artifacted ECG 111 to an analyzer 116. The analyzer 116 selects a segment of the ECG 111, generates a filtered ECG by removing the compression artifact from the selected segment the ECG 111, and determines whether the patient 102 is exhibiting a shockable rhythm (e.g., VF or pulseless V-Tach) based on the filtered ECG. In some cases, the portable defibrillator 106 outputs a recommendation 118 based on the presence or absence of the shockable rhythm in the selected segment.

In various cases, the analyzer 116 selects the segment, generates the filtered ECG, and determines whether the patient 102 exhibits the shockable rhythm over the course of an analysis period. In some examples, the analysis period includes the time period that encompasses the selected segment. The analysis period, for instance, is one second to one minute. In some implementations, the analysis period can vary based on the quality of the unfiltered ECG 111. In some cases, the analysis period is no longer than a maximum analysis period. For instance, the maximum analysis period is 10 seconds, 20 seconds, 30 seconds, one minute, or some other time period.

In the example of FIG. 1A, the analyzer 116 determines that the patient 102 is exhibiting the shockable rhythm. Thus, the analyzer 116 generates the recommendation 118 to indicate that the shock is advised. The recommendation 118 is output on the display 112, in some cases, but implementations are not so limited. In some examples, the recommendation 118 is output by an alternate output device. For example, the recommendation 118 is output by a haptic device as vibration, by a speaker as an audible signal, or a combination thereof.

The portable defibrillator 106 includes a charging circuit 120, which is inactive at the first time. For instance, a first switch 122 in the charging circuit is open, such that a battery 124 is disconnected from a capacitor 126. Once the analyzer 116 determines that the patient 102 is exhibiting the shockable rhythm, the analyzer 116 activates a charging circuit 120. Additionally or alternatively, if the analyzer 116 is unable to reach a decision (e.g., inconclusive), the analyzer 116 may still activate the charging circuit 120 in case a pause in chest compressions combined with an automated or manual analysis results in a shockable rhythm being detected thereby helping to minimize chest compression pause time.

FIG. 1B illustrates an example of the emergency environment at a second time 110B. The charging circuit 120 is active during the second time. In various cases, the first switch 122 of the active charging circuit 120 is closed, such that the battery 124 is connected to the capacitor 126. During the second time, the battery 124 is charging the capacitor 126. In some cases, the battery 124 charges the capacitor 126 up to a particular voltage associated with a defibrillation dosage appropriate for the patient 102. The portable defibrillator 106 identifies the defibrillation dosage, for example, based on an input signal from the rescuer 104 that indicates the defibrillation dosage (e.g., 200 J) or additional information such as a patient impedance measurement prior to the shock. The analyzer 116 causes the battery 124 to charge the capacitor 126 up to a voltage level that corresponds to the defibrillation dosage. In some cases, the capacitor 126 is referred to as "shock charged" when the capacitor 126 is storing sufficient voltage such that the portable defibrillator 106 is configured to and/or ready to administer the intended defibrillation dosage to the patient 102.

In various cases, a time period between the time at which the first switch 122 closes (such that the first switch 122 connects the battery 124 to the capacitor 126) and the time at which the capacitor 126 is shock charged is referred to as a "charging period" or a "charging time" of the capacitor 126. The charging period, in some cases, is seconds, tens of seconds, or longer. The charging period varies based on various conditions of the portable defibrillator 106. For example, the charging period is correlated to a charge level of the battery 124. The charging period when the battery 124 is 100% charged is shorter than when the battery 124 is 20% charged. The charging period is correlated to a temperature of the portable defibrillator 106 and/or the battery 124. The temperature is detected by a temperature sensor 128, for instance. The charging period when the temperature is moderate (e.g., at 22° C.) is longer than when the temperature is relatively cold (e.g., at 0° C.). In some examples, the portable defibrillator 106 increases the charging period when the temperature is relatively hot (e.g., at 38 C), in order to avoid overheating the battery 124. The charging period is affected by the capacitance of the capacitor 126. Although not illustrated in FIGS. 1A to 1C, in some cases, the capacitor 126 is selected by the portable defibrillator 106 among multiple capacitors with different capacitances. For instance, the capacitor 126 is selected based on the capacitance of the capacitor 126 and/or the desired defibrillation dosage to be administered to the patient 102. The charging period is positively correlated to the capacitance of the capacitor 126. The charging period is positively correlated to an output current of the battery 124. In various examples, the charging period is negatively correlated to an internal resistance of the battery 124, which reduces the output current of the battery 124. In various instances, the charging period is correlated to the desired defibrillation dosage. For example, if the desired defibrillation dosage corresponds to a relatively low charge level of the capacitor 126, then the capacitor 126 is shock charged quicker than if the desired defibrillation dosage corresponds to a relatively high charge level of the capacitor 126.

As illustrated in the example of FIG. 1B, the chest compressions are administered to the patient 102 during the second time. That is, the CPR period includes the second time. In some examples, the detection circuit 110 continues to detect the ECG 111 at the second time. The detection circuit 110 continues to provide the ECG 111 to the analyzer 116 at the second time for further analysis. The portable defibrillator 106 continues to output the ECG 111 on the display 112.

In some cases, the portable defibrillator 106 outputs a signal indicating that the capacitor 126 is shock charged. For instance, a shock element 130 of the portable defibrillator 106 includes a light that blinks when the capacitor 126 is shock charged. The capacitor 126 is shock charged when the capacitor 126 holds sufficient charge to output a defibrillation shock at the defibrillation dosage, for instance. In some examples, the portable defibrillator 106 outputs, on the display 112, a graphical user interface (GUI) element indicating that the capacitor 126 is charged. An audio signal indicating that the capacitor 126 is charged may also be used alone or in combination with other indicators.

In some implementations, it is preferable that the defibrillation shock is administered shortly after the capacitor 126 is shock charged. In some cases, capacitor 126 is imperfect and loses charge over time, even when the terminals of the capacitor are disconnected from each other (e.g., by a circuit that can conduct current). When the capacitor 126 is shock charged, the capacitor 126 remains connected to the battery 124. Accordingly, the battery 124 continues to supply energy to the capacitor 126 after the capacitor 126 is shock charged in order to replace the energy that is lost from the capacitor 126 over time. Reducing the time period between when the capacitor 126 is shock charged and when the capacitor 126 discharges the defibrillation shock therefore conserves the battery 124.

Figure 1C:
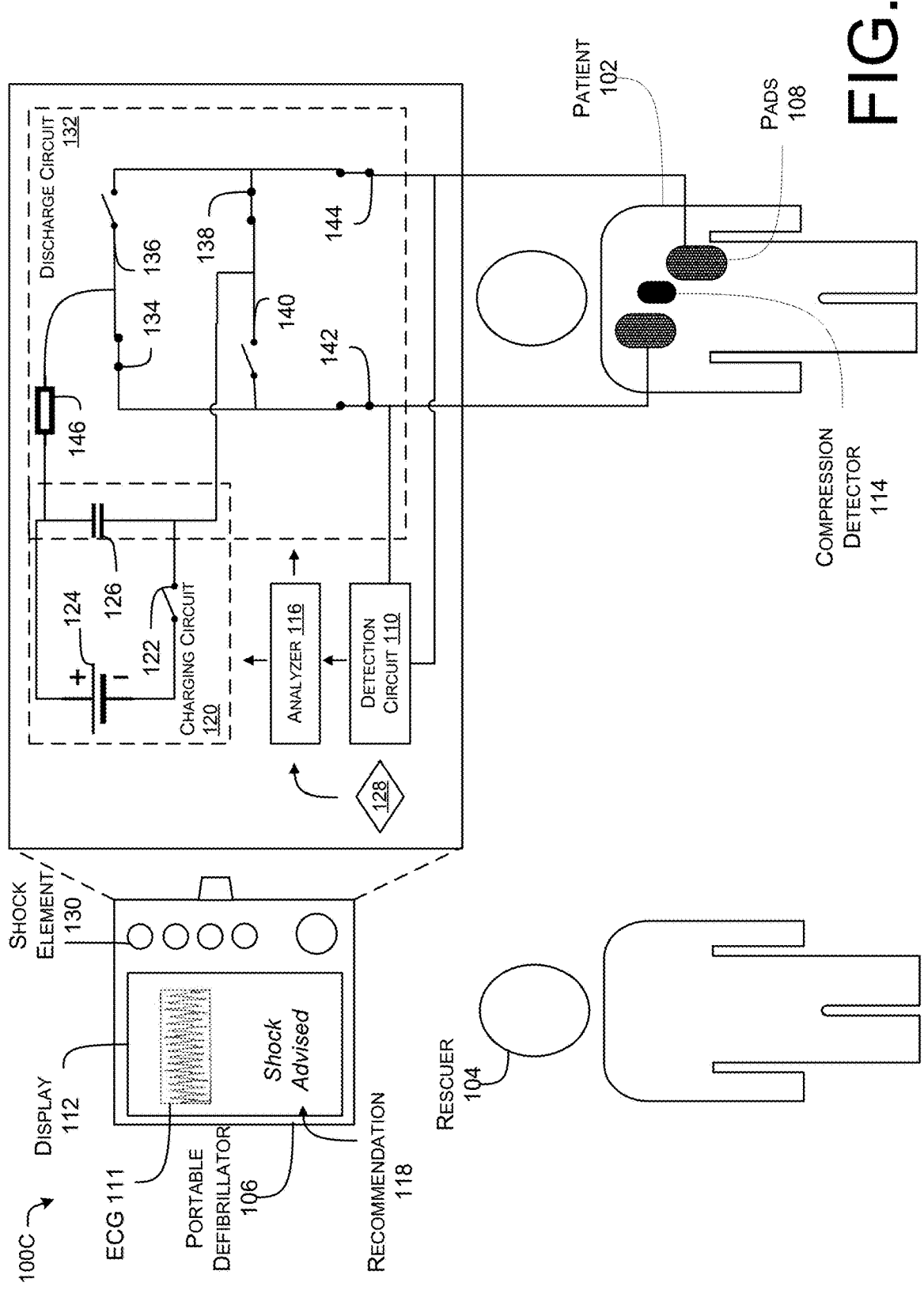

FIG. 1C illustrates an example of the emergency environment at a third time 110C. At the third time, chest compressions are no longer being administered to the patient 102. For instance, the third time is at the end or after the CPR period expires. In some cases, the shock element 130 receives an input signal (e.g., from the rescuer 104) at or before the third time.

The analyzer 116 causes the charging circuit 120 to open the first switch 122, thereby disconnecting the battery 124 from the capacitor 126. The analyzer 116 subsequently causes a discharge circuit 132 to administer a defibrillation shock to the patient 102 by discharging the charged capacitor 126. In the example of FIGS. 1A to 1C, the discharge circuit 132 includes an H-bridge that supplies the voltage from the charged capacitor 126 across defibrillation electrodes in the pads 108. The H-bridge includes a second switch 134, a third switch 136, a fourth switch 138, and a fifth switch 140. In addition, the discharge circuit 132 includes a sixth switch 142 connecting the H-bridge to a first defibrillation electrode in the pads 108 and a seventh switch 144 connecting the H-bridge to a second defibrillation electrode in the pads 108. In some examples, the discharge circuit 132 further includes a resistor 146 connected, in series, between the H-bridge and the capacitor 126. The resistor 146 is an inductive resistor, for instance. In some implementations, however, the resistor 146 is absent from the discharge circuit 132.

For example, the analyzer 116 closes the sixth switch 142 and the seventh switch 144. To administer the voltage of the defibrillation shock in a first direction, the analyzer 116 closes the second switch 134 and the fourth switch 138, leaving the third switch 136 and the fifth switch 140 open. To administer the voltage of the defibrillation shock in a second direction, the analyzer 116 closes the third switch 136 and the fifth switch 140 and opens the second switch 134 and the fourth switch 138. In some examples, a portion of the voltage stored in the capacitor 126 is administered to the patient 102 in the first direction and another portion of the voltage stored in the capacitor 126 is administered to the patient 102 in the second direction, such that the defibrillation shock administered to the patient 102 is a biphasic shock.

In various implementations described herein, the analyzer 116 initiates the analysis of the ECG 111, at the first time depicted in FIG. 1A, by predicting the CPR period, the analysis period, and/or the charging period. For example, the analyzer 116 determines a start time of the analysis based on the CPR period, the analysis period, and/or the charging period, such that the capacitor 126 is shock charged and ready to discharge the defibrillation shock when the CPR period ends. Thus, a latency period between the end of the CPR period and the time that the defibrillation shock is administered is reduced.

In various examples, the analyzer 116 predicts the end time of the CPR period. In some cases, the analyzer 116 identifies a predetermined length of the CPR period. For instance, the predetermined length is one minute, two minutes, three minutes, or another time period. The predetermined length, in some implementations, is set in advance of the first time. For example, the analyzer 116 receives an input signal from the rescuer 104, some other user, or an external device that indicates the predetermined length. In some cases, the analyzer 116 predicts the length of the CPR period based on one or more physiological parameters of the patient 102. For instance, the analyzer 116 receives and/or detects a physiological parameter (e.g., the ECG 111, an oxygenation level, a blood pressure, an airway $CO_2$ level, and/or a temperature of the patient 102) and generates the length of the CPR period based on the physiological parameter. In some cases, the analyzer 116 determines how long the patient 102 has been in cardiac arrest (e.g., based on an input signal from the rescuer 104 and/or the physiological parameter) and adjusts the length of the CPR period accordingly. The analyzer 116, for example, communicates the generated length of the CPR period to the rescuer 104. In some cases, the portable defibrillator 106 outputs the generated length of the CPR period to the user 102.

In various implementations, the analyzer 116 determines a start time of the CPR period. In some examples, the analyzer 116 automatically determines the start time of the CPR period by detecting when the chest compressions begin based on the signal from the compression detector 114, the impedance of the patient 102, and/or the ECG 111 of the patient 102. In some cases, the analyzer 116 receives an input signal from the rescuer 104, or some other user, and determines the start time of the CPR period based on the input signal. In a particular example, the display 112 is a touchscreen the portable defibrillator 106 receives a touch signal associated with a GUI element output on the display 112. The touch signal indicates the start time of the CPR period. In response to receiving the touch signal, the portable defibrillator 106 modifies the GUI element to output a countdown timer associated with the remaining time left in the CPR period, for example.

According to various examples, the analyzer 116 predicts a length of the analysis period. In some cases, the analyzer 116 predicts the length of the analysis period based on a selected analysis mode, whether the patient 102 has been previously shocked by the portable defibrillator 106 (e.g., within a particular time period), a quality of the ECG 111 that has been detected so far, a characteristic of the impedance of the patient 102, or a combination thereof. For example, the portable defibrillator 106 is operating in a continuous mode or a periodic mode. In some cases, the analysis mode of the portable defibrillator 106 is selected based on an input signal received by the portable defibrillator 106 from the rescuer 104, some other user, or an external device. In the continuous mode, the portable defibrillator 106 begins to reanalyze the ECG 111 every time a shock recommendation is made. In the periodic mode, the analyzer 116 begins to reanalyze the ECG 111 at a particular frequency. In some cases, analyzer 116 predicts the length of the analysis period to be relatively short when the portable defibrillator 106 is operating in the continuous mode and relatively long when the portable defibrillator 106 is operating in the periodic mode.

According to some implementations, the analyzer 116 predicts the length of the analysis period to be relatively short if the patient 102 has been previously shocked and relatively long if the patient 102 has not been previously shocked by the portable defibrillator 106. The analyzer 116 predicts the analysis period to be relatively short if the quality of the ECG 111 that has been detected is greater than a threshold and relatively long if the quality of the ECG 111 is less than or equal to a threshold, for example. In some instances, the analyzer 116 predicts the analysis period to be relatively short if the chest compressions are easily discernible in the impedance of the patient 102 (e.g., impedance peaks in the impedance are separated) and relatively long if the chest compressions are indiscernible in the impedance of the patient 102. In some examples, the analyzer 116 operates with a maximum length of the analysis period, and the analyzer 116 predicts that the length of the analysis period will be the maximum length. In a particular example, the maximum length of the analysis period is a length between 12 seconds and 30 seconds, such as 20 seconds.

The analyzer 116 predicts the length of the charging period, in various examples. In some cases, the analyzer 116 predicts the length of the charging period based on one or more characteristics of the battery 124, such as a charge level of the battery 124, an internal resistance of the battery 124, and/or an output current of the battery 124. In some implementations, the analyzer 116 predicts the length of the charging period based on one or more characteristics of the capacitor 126, such as a capacitance of the capacitor 126. According to some examples, the analyzer 116 predicts the charging period based on a temperature detected by the temperature sensor 128. In some implementations, the analyzer 116 predicts the charging period based on an input signal from a user (e.g., the rescuer 104). For example, the input signal specifies a defibrillation dosage (e.g., an energy, a voltage, a current, a time duration of a defibrillation shock, etc.) to be administered to the patient 102. In some cases, the analyzer 116 predicts the charging period based on one or more characteristics of the patient 102.

In various implementations, the analyzer 116 determines an end time of the predicted CPR period. The analyzer 116 determines a start time of the analysis period based on the end time of the predicted CPR period, the predicted length of the analysis period, and the predicted charging period of the capacitor 124. For instance, the start time of the analysis period is earlier than the end time of the predicted CPR period by at least the sum of the length of the predicted analysis period and the length of the predicted charging period. The start time, for instance, is during the CPR period. The analyzer 116 initiates the analysis period at the start time. Accordingly, if the analyzer 116 determines that a shockable rhythm is present in the ECG 111 during the analysis period, the analyzer 116 begins to charge the capacitor 124 during the CPR period, such that the capacitor 124 is shock charged by the end time of the predicted CPR period.

In some implementations described herein, the analyzer 116 determines whether to charge the capacitor 124 based on an analysis of a first segment of the ECG 111 and determines whether to administer the defibrillation shock based on an analysis of a second segment of the ECG 111. That is, in some examples, the analyzer 116 analyses the ECG 111 during a first analysis period and a second analysis period before determining whether to administer, or to recommend administration, of the defibrillation shock.

For example, the analyzer 116 starts the first analysis period during the CPR period and determines whether a first ECG segment associated with the first analysis period exhibits a shockable rhythm. If the shockable rhythm is exhibited, the portable defibrillator 106 begins to charge the capacitor 124. In some cases, the start time of the first analysis period is determined by the analyzer 116 such that the capacitor 124 is shock charged by the end of the CPR period.

The analyzer 116 also starts the second analysis period during the CPR period and determines whether a second ECG segment associated with the second analysis period exhibits the shockable rhythm. The start time of the second analysis period is after the start time of the first analysis period, such that the second ECG segment is associated with a later time period than the first ECG segment. In some cases, first analysis period and the second analysis period overlap. The end of the second analysis period occurs at the end of the CPR period, for example. The analyzer 116 determines whether to administer the defibrillation shock to the patient 102 based on whether the portable defibrillator 106 detects the shockable rhythm in the second ECG segment. Thus, if the patient 102 no longer exhibits the shockable rhythm, the portable defibrillator 106 recommends or prevents the defibrillation shock from being administered.

For example, the portable defibrillator 106 outputs (e.g., on the display 112) a recommendation to refrain from shocking the patient 102. In some cases, the portable defibrillator 106 automatically discharges the capacitor 126 within the circuitry of the portable defibrillator 106. For example, the analyzer 116 closes the second switch 134, the third switch 136, the fourth switch 138, and the fifth switch 140 while keeping the sixth switch 142 and the seventh switch 144 open, such that the voltage from the capacitor 126 is discharged across the resistor 146 rather than the patient 102.

In some examples, after outputting the recommendation 118 to refrain from administering the defibrillation shock based on the analysis of the second analysis period, the portable defibrillator 106 discharges the capacitor 126 to the internal circuitry of the portable defibrillator 106 or as a defibrillation shock to the patient 102 based on an input signal received from the rescuer 104. That is, the portable defibrillator 106 is operating in manual mode and is fully controlled by the rescuer 104. In some cases, the rescuer 104 may determine to administer the defibrillation shock to the patient 102 even when the analyzer 116 is unable to detect the shockable rhythm in the ECG 111. For example, the rescuer 104 may rely on an external vital sign monitor to determine that the patient 102 is likely to be experiencing a shockable rhythm and may therefore direct the portable defibrillator 106 to discharge the capacitor 126 as the defibrillation shock to the patient 102. In other examples, the rescuer 104 follows the recommendation 118 and directs the portable defibrillator 106 to discharge the energy stored in the capacitor 126 within the circuitry of the portable defibrillator 106, such that the defibrillation shock is not administered.

In some examples, the analyzer 116 adjusts the length of the CPR period based on the charging period of the capacitor 126. For instance, the analyzer 116 detects the shockable rhythm of the patient 102 at a particular time and causes the capacitor 126 to begin charging. The analyzer 116 also predicts the charging period of the capacitor 126 using any of the techniques described herein. In some cases, the analyzer 116 determines an end time of the CPR period based on the charging period of the capacitor 126. For example, the analyzer 116 determines the end time of the CPR period such that the CPR period ends immediately or shortly (e.g., within 1 second, 5 seconds, 10 seconds, or 30 seconds) after the end time of the charging period of the capacitor 126, such that the capacitor 126 is ready to be discharged when the CPR period ends. In some cases, the portable defibrillator 106 outputs a recommendation or instruction indicating the end time of the CPR period. For instance, the portable defibrillator 106 outputs a recommendation or instruction to the rescuer 104 or a mechanical chest compression device that instructs the rescuer 104 or chest compression device to administer the chest compressions until the end time of the CPR period.

Figure 2:
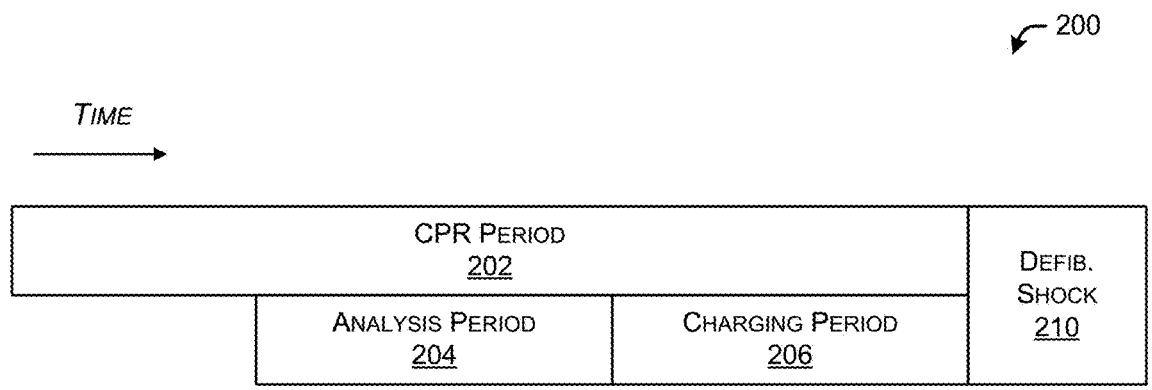
FIG. 2 illustrates an example timeline associated with pre-charging a defibrillator.

FIG. 2 illustrates an example timeline 200 associated with pre-charging a defibrillator. For example, the example timeline 200 is implemented by a medical device, such as the defibrillator, or some other computing device in communication with the defibrillator. The defibrillator, for instance, is the portable defibrillator 106 described above with reference to FIG. 1. As illustrated in FIG. 2, time increases from left to right.

The timeline 200 includes a CPR period 202. In various examples, chest compressions are administered to an individual during the CPR period 202. The chest compressions are administered by another individual (e.g., a rescuer), a chest compression device, or a combination thereof. The chest compressions are administered at greater than a particular frequency during the CPR period 202. For example, the chest compressions are administered at a frequency that is at least 1 to 3 Hz. In various examples, the chest compressions are administered during the CPR period 202 without a pause.

An analysis period 204 occurs during the CPR period 202. During the analysis period 204, the medical device detects an ECG of the individual receiving chest compressions. The medical device determines whether the ECG includes a shockable rhythm (e.g., VF or pulseless V-Tach). In various cases, the medical device performs pre-processing in order to remove a compression artifact from the ECG. For example, the medical device generates a filtered ECG by at least partially removing the compression artifact. Once the compression artifact is at least partially removed, the medical device determines whether the shockable rhythm is present in the filtered ECG. In the example illustrated in FIG. 2, the medical device determines that the shockable rhythm is present during the analysis period 204.

Based on determining that the shockable rhythm is present, the medical device initiates a charging period 206. The charging period 206 occurs after the analysis period 204 and during the CPR period 202. The medical device charges a capacitor of the defibrillator during the charging period 206. In various cases, the end of the charging period 206 occurs within a particular time period of the end of the CPR period 202. The particular time period, for instance, is a time period between 0 seconds and 30 seconds. For example, the end of the charging period 206 occurs simultaneously with the end of the CPR period 202, within a half of a second of the end of the CPR period, within a second of the end of the CPR period, within five seconds of the end of the CPR period, within ten seconds of the end of the CPR period, within 20 seconds of the end of the CPR period, or within 30 seconds of the end of the CPR period.

In the example illustrated in FIG. 2, the end of the CPR period 202 occurs simultaneously with the end of the charging period 206. A defibrillation shock 208 administered to the individual occurs after the CPR period 202 and after the charging period 206. By administering the defibrillation shock 208 after the end of the CPR period 202, the rescuer or device administering the chest compressions can avoid damage from the defibrillation shock 208. The capacitor is shock charged at the end of the charging period 206 and discharges the defibrillation shock 208. Because the charging period 206 ends simultaneously, or within a particular time period, of the CPR period 202, the defibrillation shock 208 is administered without any significant delay after the end of the CPR period 202.

In various implementations, the medical device starts the analysis period 204 at a time that ensures that charging period 206 ends simultaneously with, or within the particular time period, of the CPR period 202. For example, the medical device predicts the end time of the CPR period 202. The medical device predicts the duration of the analysis period 204. In some cases, the medical device predicts the duration of the charging period. In various examples, the medical device determines the start time of the analysis period 204 based on the end time of the CPR period 202, the duration of the analysis period 204, and the duration of the charging period 206. For instance, the medical device determines the start time of the analysis period 204 by subtracting the predicted duration of the analysis period 204 and the predicted duration of the charging period 206 from the predicted end time of the CPR period 202.

Figure 5:
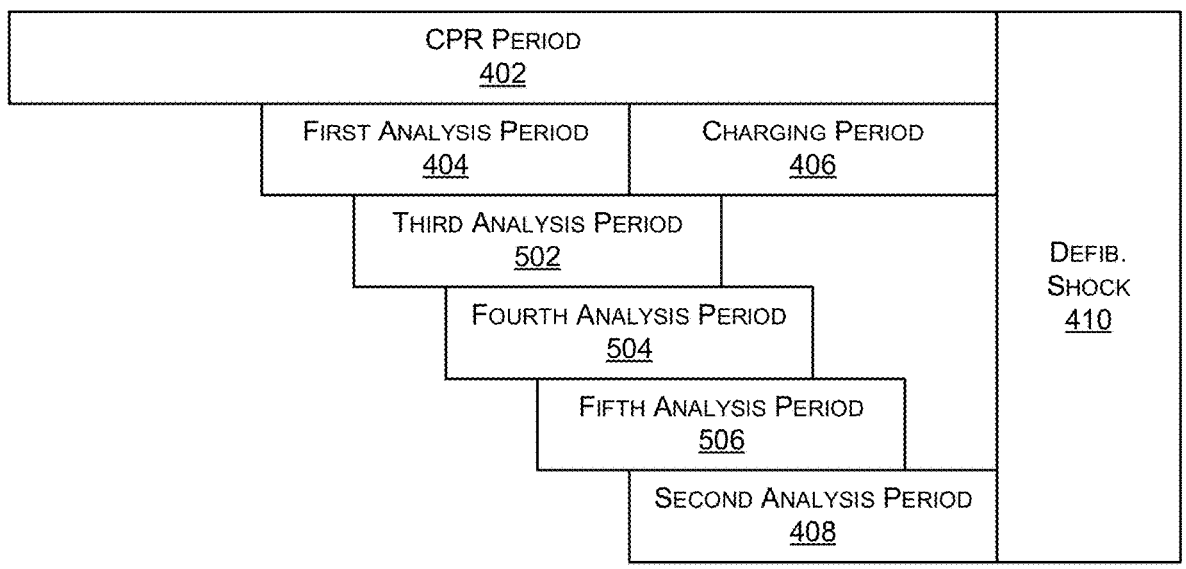
FIG. 5 illustrates another example timeline for confirming a shock recommendation by the time a capacitor of a defibrillator is charged.

Although not illustrated in FIG. 5, the charging period 406 does not necessarily have the same duration as the analysis period 504. The durations depicted in FIG. 5 are not necessarily drawn to scale.

Figure 3:
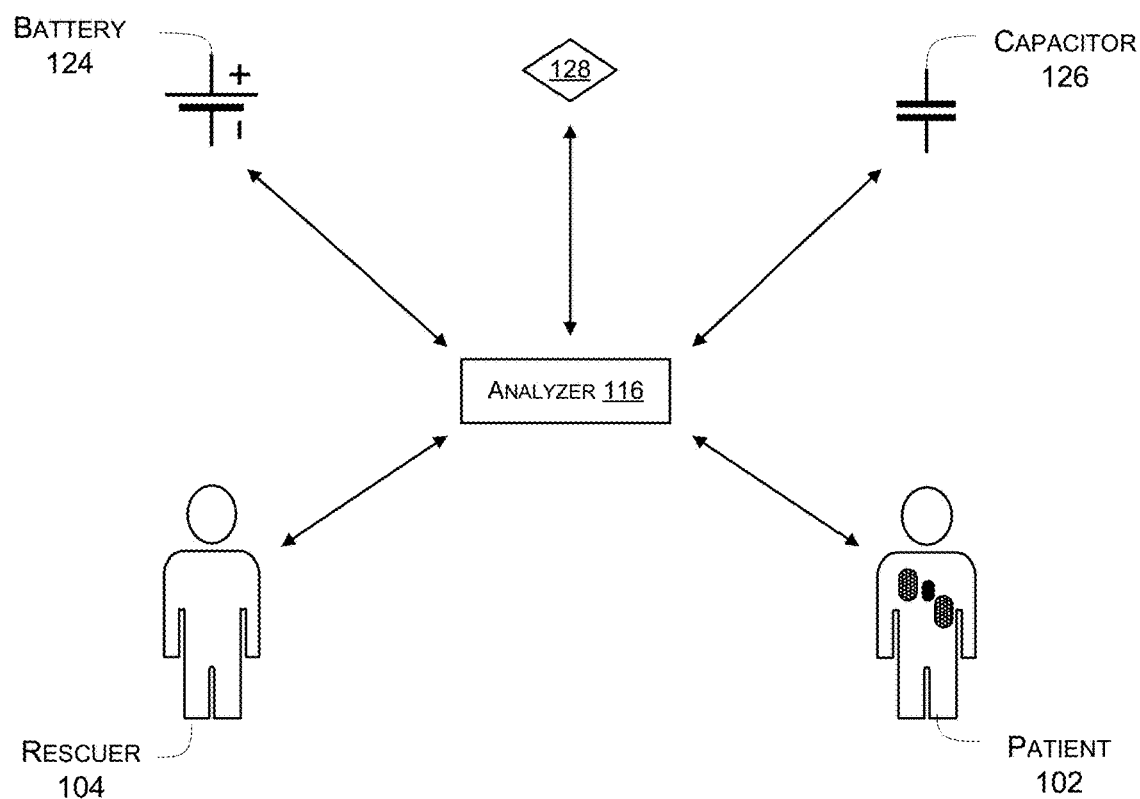
FIG. 3 illustrates various factors that an analyzer of a defibrillator uses to predict a length of a charging period of a capacitor.

FIG. 3 illustrates various factors that the analyzer 116 uses to predict a length of a charging period of the capacitor 126. As shown in FIG. 3, the analyzer 116 predicts the length of the charging period of the capacitor 126 based on parameters received from and/or associated with the battery 124, the capacitor 126, the temperature sensor 128, the patient 102, the rescuer 104, or a combination thereof.

In some cases, the analyzer 116 predicts the charging period of the capacitor 126 based on a charge level of the battery 124, an internal resistance of the battery 124, an output current of the battery 124, or a combination thereof. The charge level of the battery 124, for example, refers to the state of charge of the battery 124. In some cases, the charge level is a percentage of a current charge of the battery 124 relative to the capacity of the battery 124. The charge level of the battery 124 decreases with use (e.g., of the portable defibrillator 106). In examples in which the battery 124 is rechargeable, the charge level of the battery 124 increases when the battery 124 is recharged. As the charge level of the battery 124 decreases, the output current of the battery 124 and/or the voltage output by the battery 124 also decreases. Thus, as the charge level of the battery 124 decreases, the charging period of the capacitor 126 increases. In some cases, the analyzer 116 identifies the charge level of the battery 124 based on the output voltage of the battery 124 (which, in some cases, correlates with the charge level), integrating current output by the battery 124 over time, applying a Kalman filter to predict over-voltage based on current output by the battery 124, or a combination thereof. In accordance with Ohm's law, the internal resistance of the battery 124 is negatively correlated to the output current of the battery 124. Thus, as the internal resistance of the battery 124 increases, the charging period of the capacitor 126 increases. In some cases, the analyzer 116 determines the internal resistance of the battery 124 causing a circuit to run a current through the battery 124, identifying the magnitude of the current and the voltage of the battery 124, and dividing the voltage by the current. In some cases, the analyzer 116 determines the output current of the battery 124 based on the charge level, the voltage output by the battery 124, and/or the internal resistance of the battery 124. In some examples, the analyzer 116 estimates the output current of the battery 124 based on a previously detected output current of the battery 124. The output current of the battery 124 is negatively correlated to the charging period of the capacitor 126, in various examples.

In some implementations, the analyzer 116 predicts the charging period based on one or more characteristics of the capacitor 126. For example, the analyzer 116 identifies the capacitance of the capacitor 126 and determines the charging period based, at least in part, on the capacitance. In some cases, the analyzer 116 selects the capacitor 126 among multiple capacitors in the portable defibrillator 106. For example, the analyzer 116 selects the capacitor 126 based on a defibrillation dosage to be administered to the individual 102 being treated. The analyzer 116 measures the capacitance of the capacitor 126 using a circuit connected to the capacitor 126. In some examples, the analyzer 116 pre-stores the capacitance of the capacitor 126.

According to some examples, the analyzer 116 predicts the charging period based on the temperature detected by the temperature sensor 128. In some cases, the temperature detected by the temperature sensor 128 corresponds to the temperature of the battery 124 and/or the capacitor 126, which impacts the charging period of the capacitor 126. For example, the analyzer 116 identifies a correlation between the temperature and the output current of the battery 124. In relatively cold conditions (e.g., 0 C or less), the battery 124 outputs a relatively low output current. In relatively temperate conditions (e.g., between 0 C and 38 C), the battery 124 outputs a relatively high output current. In relatively hot temperature conditions (e.g., at 38 C or greater), the battery 124 outputs a relatively low output current to avoid overheating. The analyzer 116, for instance, determines the charging period based on the correlation and the temperature detected by the temperature sensor 128.

In some cases, the analyzer 116 predicts the charging period based on one or more input signals received from the rescuer 104. For example, the rescuer 104 selects a dosage of the defibrillation shock to be administered to the individual 102. The dosage is, for example, in units of energy (e.g., joules), in units of electric potential (e.g., volts), in units of electric current (e.g., amperes), or a combination thereof. The dosage corresponds to the charge level of the capacitor 126 when the capacitor 126 is shock charged. Thus, as the dosage increases, the charging period of the capacitor 126 also increases.

In various implementations, the analyzer 116 predicts the charging period based on at least one characteristic of the patient 102. For instance, if the patient 102 is a child (i.e., a pediatric patient), the energy of the defibrillation shock administered to the patient 102 is lower than it would be if the patient 102 was an adult. In some examples, the energy of the defibrillation shock administered to the patient 102 is related to the impedance of the individual 102 and the voltage of the defibrillation shock. If the rescuer 104 selects a dosage in units of energy (e.g., J), the analyzer 116 determines a voltage to charge the capacitor 126 based on the specified energy and the impedance of the patient 102. As the impedance of the patient 102 increases, the voltage to which the capacitor 126 is charged also increases. Thus, in some examples, the impedance of the patient 102 is positively correlated to the charging period of the capacitor 126.

Figure 4:
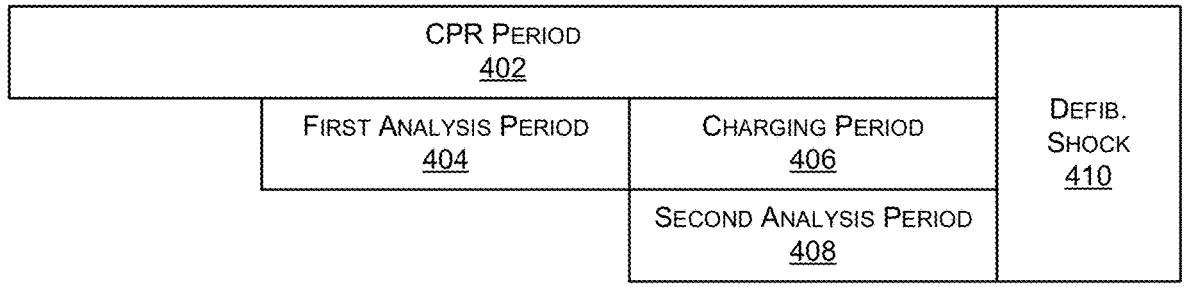
FIG. 4 illustrates an example timeline for confirming a shock recommendation by the time a capacitor of a defibrillator is charged.

FIG. 4 illustrates an example timeline 400 for confirming a shock recommendation by the time a capacitor of a defibrillator is charged. For example, the example timeline 400 is implemented by a medical device, such as the defibrillator, or some other computing device in communication with the defibrillator. The defibrillator, for instance, is the portable defibrillator 106 described above with reference to FIG. 1. As illustrated in FIG. 4, time increases from left to right.

The timeline 400 includes a CPR period 402. In various examples, chest compressions are administered to an individual during the CPR period 402. The chest compressions are administered by another individual (e.g., a rescuer), a chest compression device, or a combination thereof.

A first analysis period 404 occurs during the CPR period 402. During the first analysis period 404, the medical device detects a first segment of an ECG of the individual receiving chest compressions. The medical device determines whether the first segment includes a shockable rhythm (e.g., VF or pulseless V-Tach). In various cases, the medical device performs pre-processing in order to remove a compression artifact from the first segment. For example, the medical device generates a filtered first segment by removing at least a portion of the compression artifact from the first segment. Once the compression artifact is at least partially removed, the medical device determines whether the shockable rhythm is present in the filtered first segment. In the example illustrated in FIG. 4, the medical device determines that the shockable rhythm is present in the first segment during the first analysis period 404.

Based on determining that the shockable rhythm is present, the medical device initiates a charging period 406. The charging period 406 occurs after the first analysis period 404 and during the CPR period 402. The medical device charges a capacitor during the charging period 406. In various cases, the end of the charging period 406 occurs within a particular time period of the end of the CPR period 402. The particular time period, for instance, is a time period between 0 seconds and 30 seconds. For example, the end of the charging period 406 occurs simultaneously with the end of the CPR period 402, within a half of a second of the end of the CPR period 402, within a second of the end of the CPR period 402, within five seconds of the end of the CPR period 402, within ten seconds of the end of the CPR period 402, within 20 seconds of the end of the CPR period 402, or within 30 seconds of the end of the CPR period 402.

Additionally, a second analysis period 408 occurs as the capacitor is charging during the charging period 406. During the second analysis period 408, the medical device detects a second segment of the ECG of the individual receiving chest compressions. The medical device determines whether the second segment includes the shockable rhythm. In various cases, the medical device performs pre-processing in order to remove a compression artifact (also referred to as a "chest compression artifact") from the second segment. For example, the medical device generates a filtered second segment by removing the compression artifact from the second segment. Once the compression artifact is at least partially removed, the medical device determines whether the shockable rhythm is present in the filtered second segment. In the example illustrated in FIG. 4, the medical device determines that the shockable rhythm is present during the second analysis period 408.

Upon confirming that the shockable rhythm remains in the ECG during the second analysis period 408, the medical device recommends administration of a defibrillation shock 410 to the individual. In some examples, upon receiving an input signal from a user, the medical device discharges the charged capacitor as the defibrillation shock 410. Although not illustrated in FIG. 4, in examples in which the medical device determines that the shockable rhythm is absent from the second segment, the medical device refrains from recommending administration the defibrillation shock 410. Accordingly, if the shockable rhythm has resolved while the capacitor is being charged in the charging period 406, the medical device refrains from recommending that the defibrillation shock 410 is administered to the individual.

In some examples, the medical device administers the defibrillation shock 410 even if the medical device determines that the shockable rhythm is absent in the ECG during the second analysis period 408. For instance, the medical device outputs a recommendation against administration of the defibrillation shock. However, the medical device is operating in a manual mode, such that a user of the medical device can trigger administration of the defibrillation shock 410 even though the medical device is unable to recognize the shockable rhythm during the second analysis period 408. The user, for example, is a trained user with enough skill to identify a shockable rhythm in the ECG and/or in other physiological parameters of the individual being monitored. In some cases, the medical device discharges the charged capacitor without delivering the defibrillation shock 410 to the individual. For instance, the medical device discharges the energy stored in the capacitor across a circuit within the medical device (e.g., across a resistor) in response to receiving an input signal from the user.

Although the first analysis period 404 and the second analysis period 408 are depicted with the same duration in FIG. 4, implementations are not so limited. In addition, although the first analysis period 404 and the second analysis period 408 are illustrated as non-overlapping, implementations are not so limited. Further, the charging period 406 does not necessarily have the same duration as the first analysis period 404 and/or the second analysis period 408. The durations depicted in FIG. 4 are not necessarily drawn to scale.

FIG. 5 illustrates another example timeline 500 for confirming a shock recommendation by the time a capacitor of a defibrillator is charged. For example, the example timeline 500 is implemented by a medical device, such as the defibrillator, or some other computing device in communication with the defibrillator. The defibrillator, for instance, is the portable defibrillator 106 described above with reference to FIG. 1. As illustrated in FIG. 5, time increases from left to right.

The timeline 500 of FIG. 5 is similar to the timeline 400 of FIG. 4. However, the timeline 500 further depicts additional analysis periods that include a third analysis period 502, a fourth analysis period 504, and a fifth analysis period 506. The third analysis period 502, the fourth analysis period 504, and the fifth analysis period 506 overlap in time with the first analysis period and the second analysis period 508. For example, the timeline 500 of FIG. 5 depicts a periodic analysis of the ECG of the individual.

Once the capacitor is charged at the end of the charging period 406, the medical device relies on the most recent determination of whether the shockable rhythm is present. In the example timeline 500 of FIG. 5, the result of the second analysis period 508 is used by the medical device to determine whether to recommend that the defibrillation shock 510 should be administered to the individual. However, if the second analysis period 508 extended beyond the end of the charging period 406, the medical device would rely on the result of the fifth analysis period 506 to determine whether to recommend administration of the defibrillation shock 510, because the result of the fifth analysis period 506 would be the most recent result at the end of the charging period 406. Thus, multiple analysis periods are contemplated in some implementations of the present disclosure.

In some examples, the medical device administers the defibrillation shock 510 even if the medical device determines that the shockable rhythm is absent in the ECG during the second analysis period 508. For instance, the medical device outputs a recommendation against administration of the defibrillation shock. However, the medical device is operating in a manual mode, such that a user of the medical device can trigger administration of the defibrillation shock 510 even though the medical device is unable to recognize the shockable rhythm during the second analysis period 508. The user, for example, is a trained user with enough skill to identify a shockable rhythm in the ECG and/or in other physiological parameters of the individual being monitored. In some cases, the medical device discharges the charged capacitor without delivering the defibrillation shock 510 to the individual. For instance, the medical device discharges the energy stored in the capacitor across a circuit within the medical device (e.g., across a resistor) in response to receiving an input signal from the user.

Figure 6:
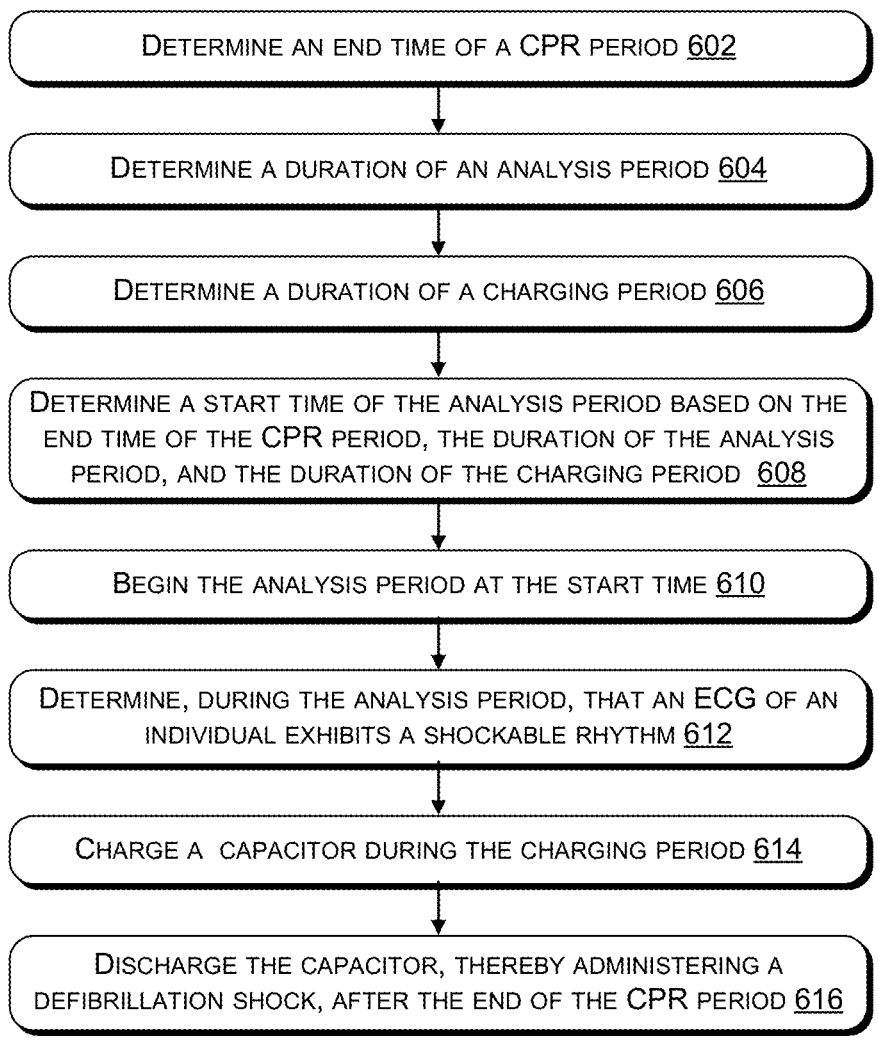
FIG. 6 illustrates an example process for pre-charging a capacitor of a defibrillator.
Figure 7:
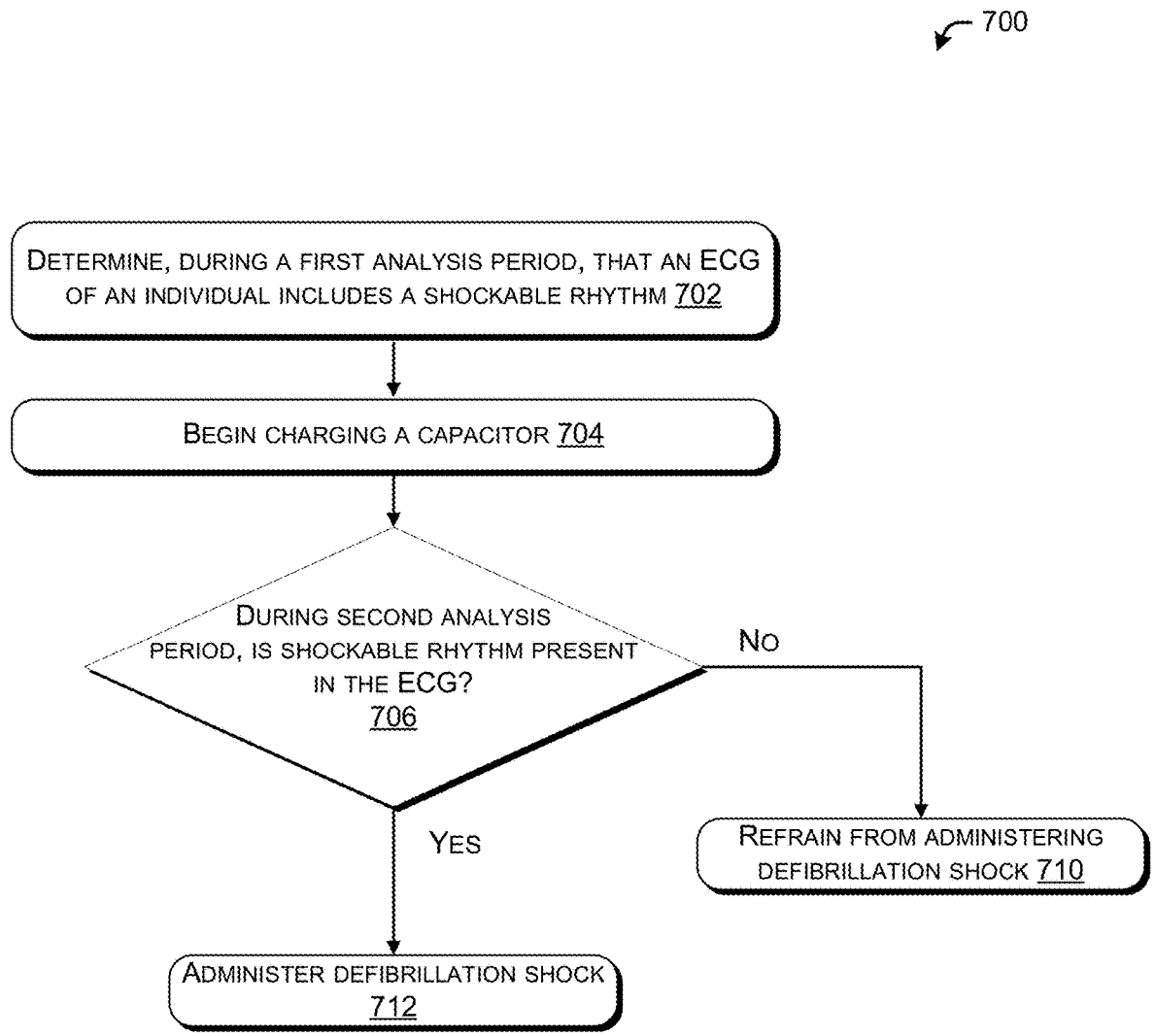
FIG. 7 illustrates an example process for confirming or updating a shock recommendation by the time a capacitor of a defibrillator is charged.
Figure 8:
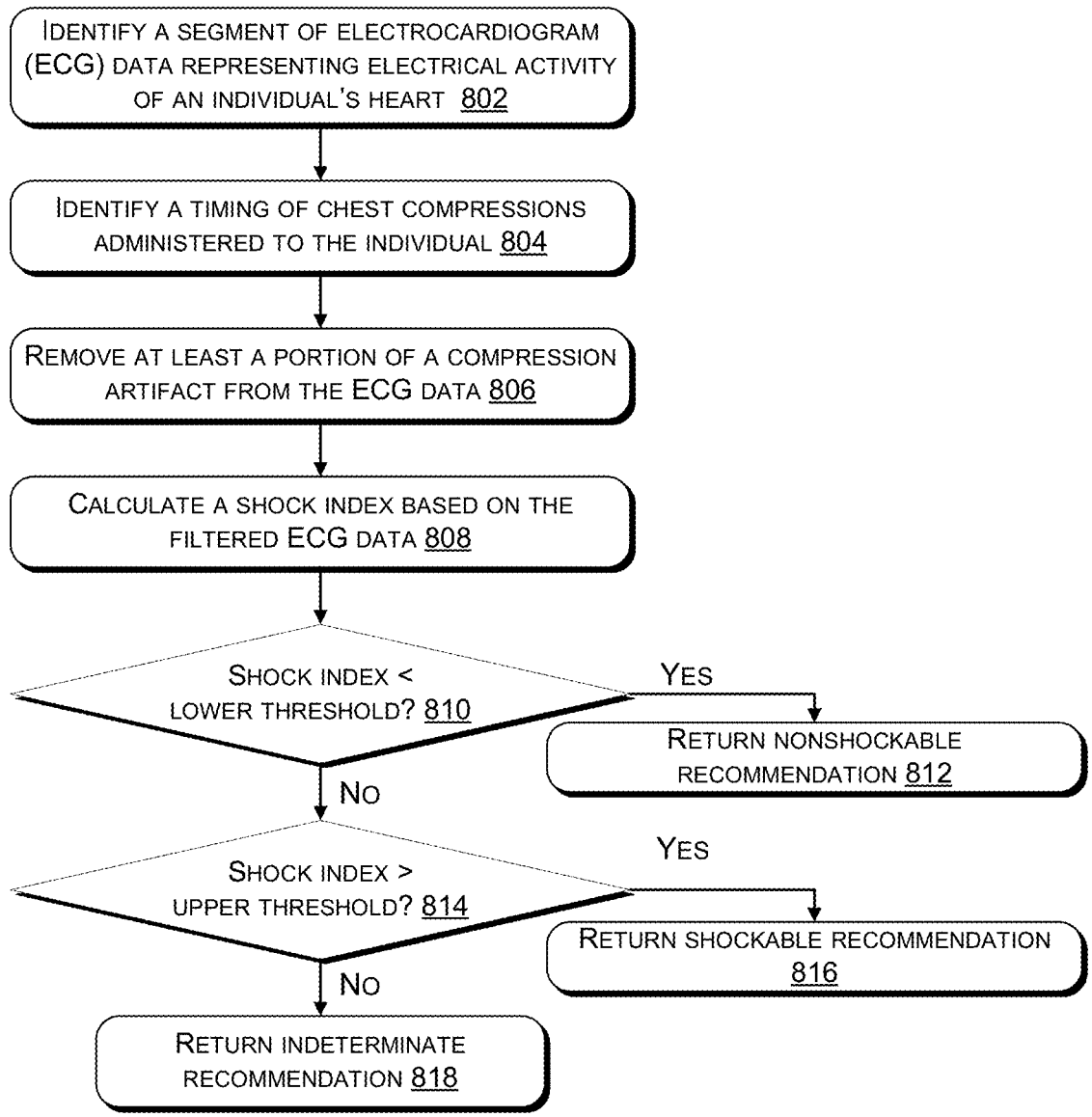
FIG. 8 illustrates an example process for determining whether a shockable rhythm is present in ECG data that includes a chest compression artifact.

FIGS. 6 to 8 illustrate processes in accordance with various implementations of the present disclosure. Although the processes in FIGS. 6 to 8 are illustrated in particular orders, implementations of the present disclosure are not necessarily limited to the particular orders depicted in FIGS. 6 to 8.

FIG. 6 illustrates an example process 600 for pre-charging a capacitor of a defibrillator. The process 600 is performed by a medical device, such as the portable defibrillator 106 described above with reference to FIG. 1.

At 602, the medical device determines (e.g., predicts) an end time of a CPR period. The CPR period is a time period during which an individual is administered chest compressions, e.g., without a pause. In some cases, the medical device determines the duration of the CPR period. The duration of the CPR period is predetermined, based on an input signal from a user, based on a parameter (e.g., a pulse detected within a time period, a previous ECG segment, etc.) of the individual being treated, or a combination thereof. For example, the CPR period has a duration of between 30 seconds and 3 minutes, such as a duration of 2 minutes. In some examples, the medical device determines the end time of the CPR period based on a start time and the duration of the CPR period. For instance, the medical device determines the start time of the CPR period based on an input signal from a user, by detecting chest compressions (e.g., via a chest compression sensor and/or an impedance of the individual), or a combination thereof.

At 604, the medical device determines (e.g., predicts) a duration of an analysis period. The analysis period is a time period during which the medical device obtains a segment of an ECG of the patient, analyzes the segment, and makes a decision about whether or not the segment includes a shockable rhythm. In various cases, the analysis period at least partially overlaps with the CPR period. The medical device, for example, determines the duration of the analysis period based on the quality of the unfiltered ECG and/or the length of previous analysis periods associated with previous analyses of the same patient. The analysis period, for instance, is one second to one minute. In some cases, the analysis period is no longer than a maximum analysis period. For instance, the maximum analysis period is 10 seconds, 20 seconds, 30 seconds, one minute, or some other time period. In some cases, the medical device predicts the length of the analysis period based on a selected analysis mode, whether the individual has been previously shocked (e.g., within a particular time period), a quality of the ECG that has been detected so far, a characteristic of the impedance of the individual, or a combination thereof.

At 606, the medical device determines (e.g., predicts) a duration of a charging period. The charging period is a time period during which the medical device charges a capacitor, such that when the charging period ends, the energy stored in the capacitor is sufficient to administer a defibrillation shock to the individual. The medical device determines the duration of the charging period, for instance, based on a capacitance of the capacitor, a charge level of a battery charging the capacitor, an internal resistance of the battery, an output current of the battery, a temperature of the medical device, a dosage level of the defibrillation shock, an impedance of the individual, a duration of a previous capacitor charge for previous charges of the capacitor (e.g., associated with previous defibrillation treatments of the same patient), or a combination thereof. The temperature is detected, for example, by one or more temperature sensors in the medical device.

At 608, the medical device determines a start time of the analysis period based on the end time of the CPR period, the duration of the analysis period, and the duration of the charging period. For instance, a time period between the start time of the analysis period and the end time of the CPR period is greater than or equal to a sum of the duration of the analysis period and the duration of the charging period. Optionally, the time period between the start time of the analysis period and the end time of the CPR period is less than or equal to a sum of a shock latency period (e.g., a time period that begins when the capacitor is shock charged and ends when the capacitor is discharged), the duration of the analysis period, and the duration of the charging period. In some examples, the shock latency period is between 0 seconds and 1 minute. For example, the shock latency period is 1 second, 5 seconds, 10 seconds, or 30 seconds.

At 610, the medical device begins the analysis period at the start time. During the analysis period, the medical device detects a segment of the ECG of the individual. The analysis period occurs during the CPR period. Thus, the ECG segment includes an artifact corresponding to the chest compressions that are administered to the individual. The medical device, in some examples, generates a filtered ECG segment by at least partially removing the chest compression artifact from the ECG segment. In some examples, the medical device calculates a shock index based on the filtered ECG segment and compares the shock index to one or more thresholds. The shock index, for example, corresponds to a certainty that the filtered ECG segment includes a shockable rhythm (e.g., VF or pulseless V-Tach).

At 612, the medical device determines, during the analysis period, that the ECG of the individual exhibits a shockable rhythm. For example, the medical device compares the shock index to a particular threshold. In some instances, the medical device determines that the ECG segment includes the shockable rhythm by determining that the shock index is greater than the particular threshold. In examples in which the shock index is negatively correlated to the certainty that the filtered ECG includes the shockable rhythm, the medical device determines that the ECG segment includes the shockable rhythm by determining that the shock index less than or equal to the particular threshold.

At 614, the medical device charges a capacitor during the charging period. The medical device, for example, begins to charge the capacitor in response to detecting the shockable rhythm at 612. That is, the charging period begins at the end of the analysis period. In some implementations, the charging period occurs during the CPR period. In some examples, the medical device begins charging the capacitor with the battery. For instance, the medical device closes a switch connecting the capacitor to the battery. Thus, electrical energy from the battery is transferred to the capacitor. In various examples, the capacitor is charged by the end time of the CPR period. For example, the capacitor stores an amount of energy associated with the defibrillation dosage by the end time of the CPR period. The capacitor may be referred to as "shock charged" at the end of the charging period.

At 616, the medical device discharges the capacitor, thereby administering a defibrillation shock, at or after the end of the CPR period. In some examples, the medical device outputs an indication, to a user, that the capacitor is charged. In some cases, the indication includes a recommendation to administer the defibrillation shock to the individual. When the medical device receives an input signal from the user, the medical device outputs the defibrillation shock. In various examples, the medical device discharges the energy stored in the capacitor to electrodes that are in contact with the individual. For example, the electrodes are placed on the chest of the individual and in contact with the individual's skin. According to some implementations, the medical device includes a discharge circuit that discharges the energy from the capacitor to the electrodes. For instance, a processor of the medical device opens the switch between the battery and the capacitor and closes one or more switches of the discharge circuit, thereby completing a circuit that includes the capacitor and the electrodes.

FIG. 7 illustrates an example process 700 for confirming or updating a shock recommendation by the time a capacitor of a defibrillator is charged. The process 700 is performed by a medical device, such as the portable defibrillator 106 described above with reference to FIG. 1.

At 702, the medical device determines, during a first analysis period, that an ECG of an individual includes a shockable rhythm. In various examples, the medical device analyzes a first segment of the ECG during the first analysis period. In some implementations, chest compressions are administered to the individual during the first analysis period, such that an artifact associated with the chest compressions is present in the first segment. The medical device, for instance, generates a filtered segment by removing at least a portion of the artifact from the first segment, determines a shock index based on the filtered segment, compares the shock index to a threshold, and determines that the shockable rhythm is present based on the comparison of the shock index to the threshold. For example, the medical device determines that the shock index exceeds the threshold. In other examples, the medical device determines that the shock index is less than or equal to the threshold. In various examples, the analysis period extends from a first time to a second time. The first time and the second time are within a CPR period, for example.

At 704, the medical device begins charging a capacitor. In some cases, the medical device begins charging the capacitor in response to determining that the first segment of the ECG includes the shockable rhythm. For instance, the medical device closes a switch connecting the capacitor to a battery. The medical device charges the capacitor based on a defibrillation dosage to be administered to the individual, in various cases.

At 706, the medical device determines, during a second analysis period, whether the shockable rhythm is present in the ECG. In various examples, the medical device analyzes a second segment of the ECG during the second analysis period. In some implementations, chest compressions are administered to the individual during the second analysis period, such that an artifact associated with the chest compressions is present in the second segment. The medical device, for instance, generates a filtered segment by removing at least a portion of the artifact from the second segment, determines a shock index based on the filtered segment, compares the shock index to a threshold, and determines whether the shockable rhythm is present based on the comparison of the shock index to the threshold. For example, the medical device determines that the shockable rhythm is present if the shock index exceeds the threshold and determines that the shockable rhythm is absent if the shock index is less than or equal to the threshold, or vice versa. In various examples, the analysis period extends from a third time to a fourth time. The third time and the fourth time are within a CPR period, for example. The third time occurs after the first time. In some examples, the third time and the fourth time occur after the second time. In some examples, the fourth time occurs within a particular time period of the end time of the CPR period. For example, the fourth time occurs within 30 seconds of the end time of the CPR period.

If the medical device determines that the shockable rhythm is absent from the ECG, the process 700 proceeds to 710. At 710, the medical device recommends against administering a defibrillation shock. In some cases, upon receiving an input signal from a user, the medical device disconnects the battery from the capacitor by opening the switch between the battery and the capacitor. In some implementations, the medical device closes one or more switches in a discharge circuit to connect the charged capacitor to an energy dissipating circuit element within the medical device, such as a resistor (e.g., an inductive resistor) in a discharge circuit. Thus, on request by the user, the energy stored in the charged capacitor is dissipated without delivering the defibrillation shock to the individual.

If, on the other hand, the medical device determines that the shockable rhythm is present in the ECG, the process 700 continues to 712. At 712, the medical device recommends administration of the defibrillation shock. In some examples, upon receiving an input signal from a user, the medical device disconnects the battery from the capacitor by opening the switch between the battery and the capacitor. In various cases, the medical device closes one or more switches in the discharge circuit to connect the charged capacitor to electrodes that are in contact with the individual. An electrical path between the electrodes, for instance, intersects the heart of the individual. The energy stored in the capacitor is discharged across the electrodes as the defibrillation shock. The defibrillation shock is administered to the heart of the individual.

In some cases, the medical device outputs a recommendation to administer the defibrillation shock. For example, the recommendation is output as a visual recommendation on a display of the medical device, a blinking light on the medical device, or the like. The medical device, for instance, receives an input signal associated the recommendation (e.g., after the recommendation is output). The input signal is received from a user, in some cases. Optionally, the medical device administers the defibrillation shock in response to receiving the input signal.

FIG. 8 illustrates an example process 800 for identifying a shockable rhythm in ECG data that includes a chest compression artifact. The process 800 is performed by a medical device, such as the portable defibrillator 106 described above with reference to FIG. 1. In some examples, the example process 800 is performed during an analysis period, such as the analysis period 204, the first analysis period 404, the second analysis period 408, the third analysis period 502, the fourth analysis period 504, or the fifth analysis period 506 described above with reference to FIGS. 2, 4, and 5.

At 802, the medical device identifies a segment of ECG data representing an electrical activity of an individual's heart when the individual is receiving chest compressions. The ECG data is obtained by detecting one or more relative voltages between electrodes connected to the chest of the individual, for instance. The ECG data is digital data representing the detected voltages, for example. According to various implementations, the chest compressions generate noise in the ECG data. The noise is at least partly based on jostling or movement of the electrodes on the skin of the individual, for example. An artifact is present in the ECG data based on the chest compressions. If the raw ECG data is output to a user, the chest compression artifact makes the ECG data difficult for the user to evaluate, in some cases. For instance, the user may have difficulty manually discerning whether a shockable rhythm (e.g., VF or pulseless V-Tach) is present in the ECG data. Accordingly, the medical device removes the artifact and automatically determines whether the shockable rhythm is present.

The segment is selected from the ECG data. As used herein, the term "segment" can refer to a subset of data that are obtained from a first time to a second time, wherein the first time occurs after the time of the first datapoint in the data and/or the second time occurs before the time of the last datapoint in the data. In some cases, the data in the segment are obtained over a time interval. The time interval, for example, is at least a minimum period and no longer than a maximum period. The minimum period, for instance, is 3 seconds, 4 seconds, 8 seconds, 10 seconds, or another time interval. The maximum period, for example, is 12 seconds, 20 seconds, 30 seconds, or some other time interval.

At 804, the medical device identifies chest compressions administered to the individual. In some cases, the medical device determines when the chest compressions are administered based on a signal from a chest compression monitor, which in some cases is disposed on the chest of the individual includes at least one accelerometer and/or gyroscope that detects chest compressions administered to the individual. In some examples, the medical device detects an electrical impedance between two or more electrodes in contact with the individual and determines when the chest compressions are administered based on the electrical impedance. The chest compressions are administered to the individual during a time period at which the segment of the ECG data is detected, such that the chest compressions cause the chest compression artifact.

At 806, the medical device generates filtered ECG data by removing the chest compression artifact of the selected segment of the ECG data. The chest compression artifact has a fundamental that is between 1.5 to 2 Hz, in various examples. However, heart rhythm features (e.g., a VF rhythm, a V-tach rhythm, QRS complexes, and other inherent heart rhythms) are typically defined by higher frequencies. In some examples, the medical device applies a filter to the detected ECG segment, such as an adaptive filter (e.g., a Wiener filter, a Kalman filter, or the like), an nth order filter (e.g., a zero-th order filter) a comb filter, an inverse comb filter, a high-pass filter, a band reject filter, a finite impulse response (FIR) filter, an infinite impulse response (IIR) filter, or a combination thereof. In some cases, the medical device converts the ECG segment from the time domain into the frequency (e.g., a Fourier) domain, a Laplace domain, a Z-transform domain, or a wavelet (e.g., a continuous wavelet transform, a discrete wavelet transform, etc.) domain, and removes at least a portion of the chest compression artifact by processing the converted ECG. According to some examples, the medical device identifies and subtracts the chest compression artifact. For instance, the medical device identifies and subtracts the chest compression artifact based on the detected chest compressions. For example, the medical device cross-correlates the ECG segment with data corresponding to the chest compressions (e.g., the impedance, the acceleration of the compression detector, the velocity of the compression detector, etc.), identifies the chest compression artifact based on the cross-correlation, and subtracts the chest compression artifact from the ECG segment. In some instances, the medical device denoises the ECG segment. For example, the medical device removes at least a portion of the chest compression artifact by performing spectral subtraction on the ECG segment.

Optionally, the medical device applies additional filtering techniques to reduce the harmonics of the chest compression artifact in the selected segment of the ECG data. For example, the medical device applies a comb filter with multiple stopbands that correspond to the fundamental frequency of the chest compressions administered to the individual and one or more harmonics of the fundamental frequency.

At 808, the medical device calculates a shock index based on the filtered ECG data. The shock index, for example, corresponds to a likelihood that the original ECG data and/or the filtered ECG data exhibits a rhythm that is treatable with defibrillation. For example, the shock index relates to the likelihood that the filtered ECG data is indicative that the individual is exhibiting VF or pulseless V-Tach. In some examples, the medical device calculates the shock index by detecting a shockable rhythm (e.g., VF or pulseless V-Tach) in the filtered ECG data. In some cases, the medical device performs a rules-based analysis on the filtered ECG data. In some examples, the shock index is generated based on an amplitude magnitude spectrum area (AMSA) of the filtered ECG data, an amplitude of the filtered ECG data, a frequency of the filtered ECG data, or a combination thereof. In some implementations, the medical device calculates the shock index by determining a spectral similarity between the filtered ECG and a sample ECG with a known shockable rhythm (e.g., VF or pulseless V-Tach) and/or by determining a spectral dissimilarity between the filtered ECG and a sample ECG with a known nonshockable rhythm (e.g., asystole, a sinus rhythm including QRS complexes, etc.). In some examples the medical device uses non-ECG data to generate the shock index, at least in part. For instance, the medical device generates the shock index based on a non-ECG physiological parameter (e.g., a heart rate level or waveform, a temperature level or waveform, an airway $CO_2$ level or waveform, an oxygenation level or waveform, a blood pressure level or waveform, etc.) of the individual, a type of equipment monitoring the individual, a demographic of the individual, or a combination thereof. In some examples, the shock index is calculated based on a regression (e.g., linear regression, binary regression, polynomial regression, logistic regression, nonlinear regression, nonparametric regression, etc.) model outputting a probability that the filtered ECG exhibits a shockable rhythm based on one or more characteristics of the filtered ECG. In various implementations, the medical device generates the shock index based on one or more analysis factors.

At 810, the medical device determines whether the shock index is less than a lower threshold. The lower threshold is selected, for instance, based on an acceptable level of uncertainty regarding a nonshockable recommendation. In some cases, the lower threshold is user-selected, such that the lower threshold is calculated based on an input signal from a user. In some cases, the lower threshold is determined based on one or more analysis factors. If the medical device determines that the shock index is less than the lower threshold, the medical device returns a nonshockable recommendation at 812.

If, on the other hand, the medical device determines that the shock index is greater than or equal to the lower threshold, the process 800 proceeds to 814. At 814, the medical device determines whether the shock index is greater than the upper threshold. The upper threshold is selected, for instance, based on an acceptable level of uncertainty regarding a shockable recommendation. In some cases, the upper threshold is user-selected, such that the upper threshold is calculated based on an input signal from a user. In some examples, the upper threshold is determined based on one or more analysis factors. If the medical device determines that the shock index is greater than the upper threshold, the medical device returns a shockable recommendation at 816.

However, if the medical device determines that the shock index is less than or equal to the upper threshold, then the medical device returns an indeterminate recommendation at 818. The indeterminate decision means that the medical device is unable to conclude whether the shockable rhythm is present with a sufficient level of certainty. The level of certainty, in some cases, is predetermined and/or selected by a user.

In various cases, the medical device performs the process 800 repeatedly, periodically, or a combination thereof. For example, upon returning a recommendation, the medical device repeats the process 800 by identifying another segment of ECG data. In some cases, the medical device initiates the process 800 (e.g., begins 802) at a particular frequency, such that the medical device may be performing the process 800 multiple times, in parallel, at a time. If the medical device determines multiple recommendations based on repeatedly and/or periodically performing the process 800, the medical device outputs (e.g., to the user) a recommendation based on the most recently returned shock decision.

Figure 9:
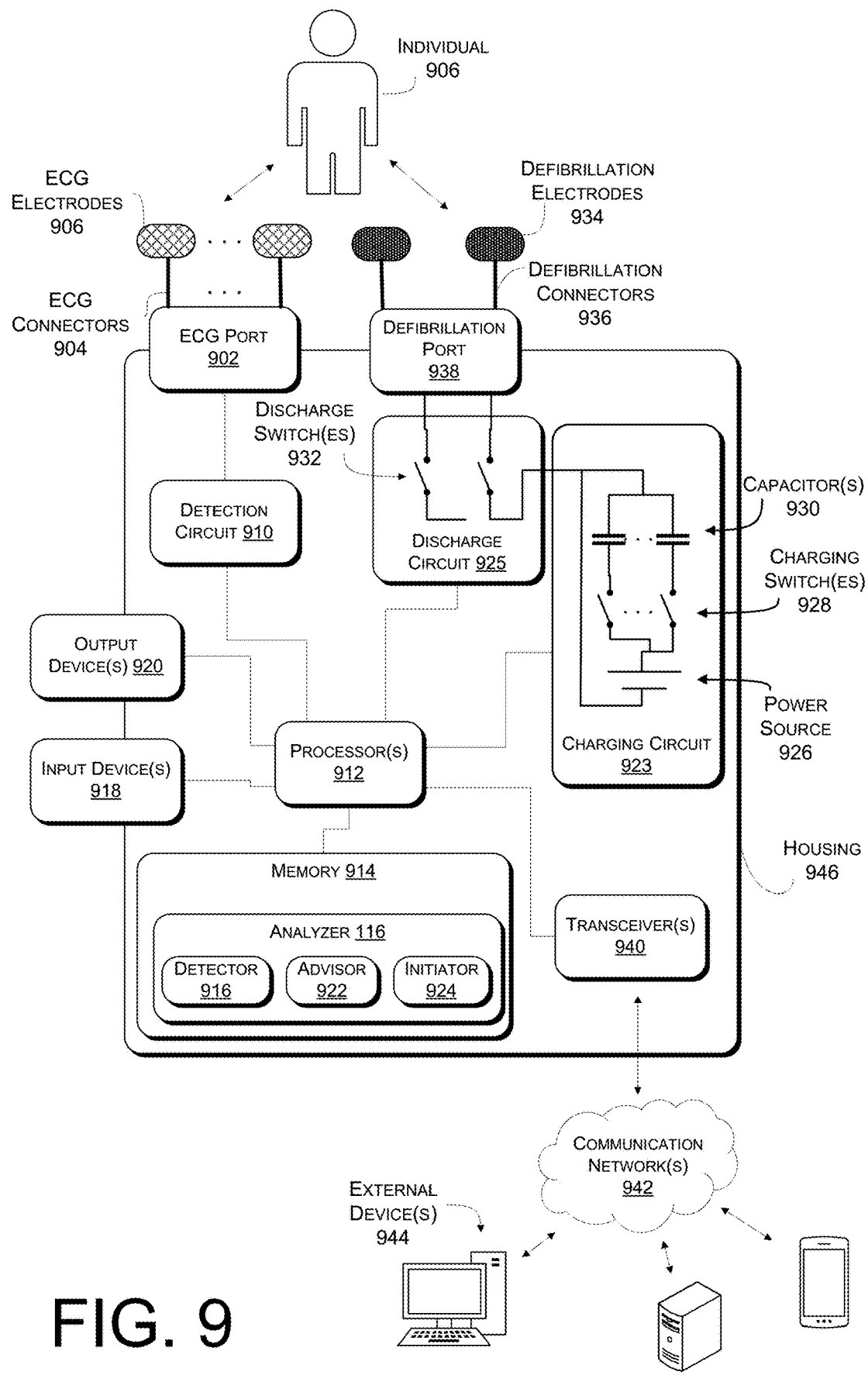
FIG. 9 illustrates an example of an external defibrillator configured to perform various functions described herein.

FIG. 9 illustrates an example of an external defibrillator 900 configured to perform various functions described herein. For example, the external defibrillator 900 is the portable defibrillator 106 described above with reference to FIG. 1.

The external defibrillator 900 includes an electrocardiogram (ECG) port 902 connected to multiple ECG connectors 904. In some cases, the ECG connectors 904 are removeable from the ECG port 902. For instance, the ECG connectors 904 are plugged into the ECG port 902. The ECG connectors 904 are connected to ECG electrodes 906, respectively. In various implementations, the ECG electrodes 906 are disposed on different locations on an individual 908. A detection circuit 910 is configured to detect relative voltages between the ECG electrodes 906. These voltages are indicative of the electrical activity of the heart of the individual 908.

In various implementations, the ECG electrodes 906 are in contact with the different locations on the skin of the individual 908. In some examples, a first one of the ECG electrodes 906 is placed on the skin between the heart and right arm of the individual 908, a second one of the ECG electrodes 906 is placed on the skin between the heart and left arm of the individual 908, and a third one of the ECG electrodes 906 is placed on the skin between the heart and a leg (either the left leg or the right leg) of the individual 908. In these examples, the detection circuit 908 is configured to measure the relative voltages between the first, second, and third ECG electrodes 906. Respective pairings of the ECG electrodes 906 are referred to as "leads," and the voltages between the pairs of ECG electrodes 906 are known as "lead voltages." In some examples, more than three ECG electrodes 906 are included, such that 5-lead or 12-lead ECG signals are detected by the detection circuit 910.

The detection circuit 910 includes at least one analog circuit, at least one digital circuit, or a combination thereof. The detection circuit 910 receives the analog electrical signals from the ECG electrodes 906, via the ECG port 902 and the ECG connectors 904. In some cases, the detection circuit 910 includes one or more analog filters configured to filter noise and/or artifact from the electrical signals. The detection circuit 910 includes an analog-to-digital (ADC) in various examples. The detection circuit 910 generates a digital signal indicative of the analog electrical signals from the ECG electrodes 906. This digital signal can be referred to as an "ECG signal" or an "ECG."

In some cases, the detection circuit 910 further detects an electrical impedance between at least one pair of the ECG electrodes 906. For example, the detection circuit 910 includes, or otherwise controls, a power source that applies a known voltage across a pair of the ECG electrodes 906 and detects a resultant current between the pair of the ECG electrodes 906. The impedance is generated based on the applied voltage and the resultant current. In various cases, the impedance corresponds to respiration of the individual 908, chest compressions performed on the individual 908, and other physiological states of the individual 908. In various examples, the detection circuit 910 includes one or more analog filters configured to filter noise and/or artifact from the resultant current. The detection circuit 910 generates a digital signal indicative of the impedance using an ADC. This digital signal can be referred to as an "impedance signal" or an "impedance."

The detection circuit 910 provides the ECG signal and/or the impedance signal one or more processors 912 in the external defibrillator 900. In some implementations, the processor(s) 912 includes a central processing unit (CPU), a graphics processing unit (GPU), both CPU and GPU, or other processing unit or component known in the art.

The processor(s) 912 is operably connected to memory 914. In various implementations, the memory 912 is volatile (such as random access memory (RAM)), non-volatile (such as read only memory (ROM), flash memory, etc.) or some combination of the two. The memory 914 stores instructions that, when executed by the processor(s) 912, causes the processor(s) 912 to perform various operations. In various examples, the memory 914 stores methods, threads, processes, applications, objects, modules, any other sort of executable instruction, or a combination thereof. In some cases, the memory 914 stores files, databases, or a combination thereof. In some examples, the memory 914 includes, but is not limited to, RAM, ROM, electrically erasable programmable read-only memory (EEPROM), flash memory, or any other memory technology. In some examples, the memory 914 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 912 and/or the external defibrillator 900. In some cases, the memory 914 at least temporarily stores the ECG signal and/or the impedance signal. The memory 914, for example, stores instructions enabling the capacitor(s) 912 to perform operations of the analyzer 116 described above with reference to FIG. 1.

In various examples, the memory 914 includes a detector 916, which causes the processor(s) 912 to determine, based on the ECG signal and/or the impedance signal, whether the individual 908 is exhibiting a particular heart rhythm. For instance, the processor(s) 912 determines whether the individual 908 is experiencing a shockable rhythm that is treatable by defibrillation. Examples of shockable rhythms include ventricular fibrillation (VF) and pulseless ventricular tachycardia (V-Tach). In some examples, the processor(s) 912 determines whether any of a variety of different rhythms (e.g., asystole, sinus rhythm, atrial fibrillation (AF), etc.) are present in the ECG signal.

The processor(s) 912 is operably connected to one or more input devices 918 and one or more output devices 920. Collectively, the input device(s) 918 and the output device(s) 920 function as an interface between a user and the defibrillator 900. The input device(s) 918 is configured to receive an input from a user and includes at least one of a keypad, a cursor control, a touch-sensitive display (e.g., a touchscreen), a voice input device (e.g., a speaker), a haptic feedback device, or any combination thereof. The output device(s) 920 includes at least one of a display, a speaker, a haptic output device, a printer, or any combination thereof. In various examples, the processor(s) 912 causes a display among the input device(s) 918 to visually output a waveform of the ECG signal and/or the impedance signal. In some implementations, the input device(s) 918 includes one or more touch sensors, the output device(s) 920 includes a display screen, and the touch sensor(s) are integrated with the display screen. Thus, in some cases, the external defibrillator 900 includes a touchscreen configured to receive user input signal(s) and visually output physiological parameters, such as the ECG signal and/or the impedance signal.

In some examples, the memory 914 includes an advisor 922, which, when executed by the processor(s) 912, causes the processor(s) 912 to generate advice and/or control the output device(s) 920 to output the advice to a user (e.g., a rescuer). In some examples, the processor(s) 912 provides, or causes the output device(s) 920 to provide, an instruction to perform CPR on the individual 908. In some cases, the processor(s) 912 evaluates, based on the ECG signal, the impedance signal, or other physiological parameters, CPR being performed on the individual 908 and causes the output device(s) 920 to provide feedback about the CPR in the instruction. According to some examples, the processor(s) 912, upon identifying that a shockable rhythm is present in the ECG signal, causes the output device(s) 920 to output an instruction and/or recommendation to administer a defibrillation shock to the individual 908.

The memory 914 also includes an initiator 924 which, when executed by the processor(s) 912, causes the processor(s) 912 to control other elements of the external defibrillator 900 in order to administer a defibrillation shock to the individual 908. In some examples, the processor(s) 912 executing the initiator 924 selectively causes the administration of the defibrillation shock based on determining that the individual 908 is exhibiting the shockable rhythm and/or based on an input from a user (received, e.g., by the input device(s) 918. In some cases, the processor(s) 912 causes the defibrillation shock to be output at a particular time, which is determined by the processor(s) 912 based on the ECG signal and/or the impedance signal. The analyzer 116 includes the detector 916, the advisor 922, and the imitator 924, for example.

The processor(s) 912 is operably connected to a charging circuit 923 and a discharge circuit 925. In various implementations, the charging circuit 923 includes a power source 926, one or more charging switches 928, and one or more capacitors 930. The power source 926 includes, for instance, a battery. The processor(s) 912 initiates a defibrillation shock by causing the power source 926 to charge at least one capacitor among the capacitor(s) 930. For example, the processor(s) 912 activates at least one of the charging switch(es) 928 in the charging circuit 923 to complete a first circuit connecting the power source 926 and the capacitor to be charged. Then, the processor(s) 912 causes the discharge circuit 925 to discharge energy stored in the charged capacitor across a pair of defibrillation electrodes 930, which are in contact with the individual 908. For example, the processor(s) 912 deactivates the charging switch(es) 928 completing the first circuit between the capacitor(s) 930 and the power source 926, and activates one or more discharge switches 932 completing a second circuit connecting the charged capacitor 930 and at least a portion of the individual 908 disposed between defibrillation electrodes 934. Although not illustrated in FIG. 9, in some implementations, the discharge circuit 925 includes an H-bridge over which the energy from the capacitor(s) 930 is discharged across the defibrillation electrodes 930.

The energy is discharged from the defibrillation electrodes 934 in the form of a defibrillation shock. For example, the defibrillation electrodes 934 are connected to the skin of the individual 908 and located at positions on different sides of the heart of the individual 908, such that the defibrillation shock is applied across the heart of the individual 908. The defibrillation shock, in various examples, depolaries a significant number of heart cells in a short amount of time. The defibrillation shock, for example, interrupts the propagation of the shockable rhythm (e.g., VF or pulseless V-Tach) through the heart. In some examples, the defibrillation shock is 200 J or greater with a duration of about 0.015 seconds. In some cases, the defibrillation shock has a multiphasic (e.g., biphasic) waveform. The discharge switch(es) 932 are controlled by the processor(s) 912, for example. In various implementations, the defibrillation electrodes 934 are connected to defibrillation connectors 936. The defibrillation connectors 936 are connected to a defibrillation port 938, in implementations. According to various examples, the defibrillation connectors 936 are removable from the defibrillation port 938. For example, the defibrillation connectors 936 are plugged into the defibrillation port 938.

In various implementations, the processor(s) 912 is operably connected to one or more transceivers 940 that transmit and/or receive data over one or more communication networks 942. For example, the transceiver(s) 940 includes a network interface card (NIC), a network adapter, a local area network (LAN) adapter, or a physical, virtual, or logical address to connect to the various external devices and/or systems. In various examples, the transceiver(s) 940 includes any sort of wireless transceivers capable of engaging in wireless communication (e.g., radio frequency (RF) communication). For example, the communication network(s) 942 includes one or more wireless networks that include a $3^{rd}$ Generation Partnership Project (3GPP) network, such as a Long Term Evolution (LTE) radio access network (RAN) (e.g., over one or more LE bands), a New Radio (NR) RAN (e.g., over one or more NR bands), or a combination thereof. In some cases, the transceiver(s) 940 includes other wireless modems, such as a modem for engaging in WI-FI®, WIGIG®, WIMAX®, BLUETOOTH®, or infrared communication over the communication network(s) 942.

The defibrillator 900 is configured to transmit and/or receive data (e.g., ECG data, impedance data, data indicative of one or more detected heart rhythms of the individual 908, data indicative of one or more defibrillation shocks administered to the individual 908, etc.) with one or more external devices 944 via the communication network(s) 942. The external devices 944 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 942. In some examples, the external device(s) 944 is located remotely from the defibrillator 900, such as at a remote clinical environment (e.g., a hospital). According to various implementations, the processor(s) 912 causes the transceiver(s) 940 to transmit data to the external device(s) 944. In some cases, the transceiver(s) 940 receives data from the external device(s) 944 and the transceiver(s) 940 provide the received data to the processor(s) 912 for further analysis.

In various implementations, the external defibrillator 900 also includes a housing 946 that at least partially encloses other elements of the external defibrillator 900. For example, the housing 946 encloses the detection circuit 910, the processor(s) 912, the memory 914, the charging circuit 923, the transceiver(s) 940, or any combination thereof. In some cases, the input device(s) 918 and output device(s) 920 extend from an interior space at least partially surrounded by the housing 946 through a wall of the housing 946. In various examples, the housing 946 acts as a barrier to moisture, electrical interference, and/or dust, thereby protecting various components in the external defibrillator 900 from damage.

In some implementations, the external defibrillator 900 is an automated external defibrillator (AED) operated by an untrained user (e.g., a bystander, layperson, etc.) and can be operated in an automatic mode. In automatic mode, the processor(s) 912 automatically identifies a rhythm in the ECG signal, makes a decision whether to administer a defibrillation shock, charges the capacitor(s) 930, discharges the capacitor(s) 930, or any combination thereof. In some cases, the processor(s) 912 controls the output device(s) 920 to output (e.g., display) a simplified user interface to the untrained user. For example, the processor(s) 912 refrains from causing the output device(s) 920 to display a waveform of the ECG signal and/or the impedance signal to the untrained user, in order to simplify operation of the external defibrillator 900.

In some examples, the external defibrillator 900 is a monitor-defibrillator utilized by a trained user (e.g., a clinician, an emergency responder, etc.) and can be operated in a manual mode or the automatic mode. When the external defibrillator 900 operates in manual mode, the processor(s) 912 cause the output device(s) 920 to display a variety of information that may be relevant to the trained user, such as waveforms indicating the ECG data and/or impedance data, notifications about detected heart rhythms, and the like.

Example Clauses

1. An external defibrillator, including: a detection circuit configured to detect an electrocardiogram (ECG) of an individual; a capacitor; a battery configured to charge the capacitor; a discharge circuit configured to discharge the capacitor; a processor; and memory storing instructions that, when executed by the processor, cause the processor to perform operations including: identifying an end time of a cardiopulmonary resuscitation (CPR) period, wherein the individual is receiving chest compressions during the CPR period; predicting a duration of a charging period of the capacitor based on a charge level of the battery, a capacitance of the capacitor, a temperature of the external defibrillator, and a dosage level of a defibrillation shock; determining, based on the end time of the CPR period and the duration of the charging time of the capacitor, a start time of an analysis period; identifying a segment of the ECG obtained during the analysis period, the analysis period occurring between the start time and an intermediate time; generating a filtered ECG by removing a chest compression artifact from the segment of the ECG; determining that the filtered ECG exhibits ventricular fibrillation (VF); in response to determining that the filtered ECG exhibits the VF, causing the battery to charge the capacitor during the charging period such that the capacitor is charged at the end time of the CPR period; and causing the discharge circuit to discharge energy stored in the capacitor to the individual as the defibrillation shock at the end of the CPR period.

2. The external defibrillator of clause 1, further including: a display configured to visually output a recommendation; an input device configured to receive an input signal from a user, wherein the operations further include: generating the recommendation based on determining that the filtered ECG exhibits the shockable rhythm, and wherein causing the discharge circuit to discharge the energy stored in the capacitor to the individual is in response to the input device receiving the input signal.

3. The external defibrillator of clause 1 or 2, wherein a time period between the start time of the analysis period and the end time of the CPR period is greater than or equal to a sum of the charging period and the analysis period.

4. A medical device, including: a detection circuit configured to detect an electrocardiogram (ECG) of an individual; a capacitor; a battery configured to charge the capacitor; a processor; and memory storing instructions that, when executed by the processor, cause the processor to perform operations including: identifying an end time of a cardiopulmonary resuscitation (CPR) period, the individual receiving chest compressions during the CPR period; determining a length of a charging period of the capacitor based on a charge level of the battery; determining, based on the length of the charging period of the capacitor, a start time of an analysis period; identifying, during the analysis period and the CPR period, a segment of the ECG; determining that the segment of the ECG includes a shockable rhythm; and in response to determining that the segment of the ECG includes the shockable rhythm, causing the battery to charge the capacitor such that the capacitor is charged at the end time of the CPR period.

5. The medical device of clause 4, further including: a temperature sensor configured to detect a temperature of the medical device, wherein determining the length of the charging period of the capacitor is based on a capacitance of the capacitor, an internal resistance of the battery, the temperature of the medical device, a dosage level of a defibrillation shock, an impedance of the individual, or a combination thereof.

6. The medical device of clause 4 or 5, wherein the operations further include: predicting a length of the analysis period, wherein determining the start time of the analysis period is further based on the length of the analysis period.

7. The medical device of any one of clauses 4 to 6, wherein determining that the segment of the ECG includes the shockable rhythm includes: generating a filtered ECG by removing a chest compression artifact from the segment of the ECG; generating a shock index based on the filtered ECG; and comparing the shock index to a threshold.

8. The medical device of any one of clauses 4 to 7, wherein the capacitor is charged within ten seconds before the end time of the CPR period.

9. The medical device of any one of clauses 4 to 8, wherein a time period between the start time of the analysis period and the end time of the CPR period is greater than or equal to a sum of the length of the charging period and a length of the analysis period.

10. The medical device of any one of clauses 4 to 9, further including: a discharge circuit configured to discharge the capacitor; and electrodes connected to the skin of the individual, wherein the operations further include: causing the discharge circuit to discharge energy stored in the charged capacitor to the electrodes.

11. The medical device of clause 10, further including: an output device configured to output a recommendation to administer a defibrillation shock; and an input device configured to receive an input signal, wherein the operations further include: determining that the capacitor is charged; based on determining that the capacitor is charged, causing the output device to output the recommendation to administer the defibrillation shock; and receiving an input signal based on the recommendation, and wherein causing the discharge circuit to discharge the energy stored in the charged capacitor to the electrodes is in response to receiving the input signal.

12. The medical device of clause 10 or 11, wherein the discharge circuit includes first switches, and wherein causing the discharge circuit to discharge the energy stored in the charged capacitor to the electrodes includes: disconnecting the battery from the capacitor by opening a second switch; and connecting the capacitor to the electrodes by closing the first switches in the discharge circuit.

13. A method performed by a medical device, the method including: identifying an end time of a cardiopulmonary resuscitation (CPR) period, wherein an individual is receiving chest compressions during the CPR period; determining, based on a charge level of a battery, a length of a charging period of a capacitor of the medical device; determining, based on the end time of the CPR period and the length of the charging period of the capacitor, a start time of an analysis period that overlaps the CPR period; identifying, during the analysis period, a segment of an electrocardiogram (ECG) of the individual; determining that the segment of the ECG includes a shockable rhythm; and based on determining that the segment of the ECG includes the shockable rhythm, charging the capacitor during the charging period by connecting the battery to the capacitor, the capacitor being charged at the end time of the CPR period.

14. The method of clause 13, wherein determining the charging period of the capacitor includes determining a capacitance of the capacitor, determining an internal resistance of the battery, determining a temperature of the medical device, determining a dosage level of a defibrillation shock, determining an impedance of the individual, or a combination thereof.

15. The method of clause 13 or 14, further including: determining a length of the analysis period, wherein determining the start time of the analysis period is further based on the length of the analysis period.

16. The method of any one of clauses 13 to 15, wherein determining that the segment of the ECG includes the shockable rhythm includes: generating a filtered ECG by removing a chest compression artifact from the segment of the ECG; generating a shock index based on the filtered ECG; and comparing the shock index to a threshold.

17. The method of any one of clauses 13 to 16, wherein the capacitor is charged within ten seconds before the end time of the CPR period.

18. The method of any one of clauses 13 to 17, wherein a time period between the start time of the analysis period and the end time of the CPR period is greater than or equal to a sum of the length of the charging period and a length of the analysis period.

19. The method of any one of clauses 13 to 18, further including: administering a defibrillation shock to the individual by discharging the charged capacitor.

20. The method of clause 19, further including: outputting a recommendation to administer the defibrillation shock; and receiving an input signal based on the recommendation, wherein administering the defibrillation shock to the individual by discharging the capacitor is in response to receiving the input signal.

21. An external defibrillator, including: a detection circuit configured to detect an electrocardiogram (ECG) of an individual; a capacitor; a battery; an output device; a processor; and memory storing instructions that, when executed by the processor, cause the processor to perform operations including: identifying a first segment of the ECG of the individual, the first segment extending from a first time to a second time and being obtained when the individual is receiving first chest compressions; determining that the first segment includes ventricular fibrillation (VF); based on determining that the first segment includes the VF, causing the battery to charge the capacitor; identifying a second segment of the individual, the second segment extending from a third time to a fourth time and being obtained when the individual is receiving second chest compressions; determining that the VF is present in the second segment; and based on determining that the VF is present in the second segment, causing the output device to output a recommendation to administer a defibrillation shock to the individual.

22. The external defibrillator of clause 21, wherein determining that the first segment includes the VF includes: generating a filtered ECG by removing, from the first segment, an artifact corresponding to the first chest compressions; generating a shock index based on the filtered ECG; and determining that the shock index is greater than a threshold.

23. The external defibrillator of clause 21 or 22, further including: an input device configured to receive an input signal from a user; electrodes attached to the skin of the individual; and a discharge circuit configured to discharge the capacitor, wherein the operations further include: based on the input signal, causing the external defibrillator to administer the defibrillation shock by causing the discharge circuit to discharge the capacitor to the electrodes.

24. A medical device, including: a detection circuit configured to detect an electrocardiogram (ECG) of an individual; a capacitor; a battery configured to charge the capacitor; a processor; and memory storing instructions that, when executed by the processor, cause the processor to perform operations including: identifying a first segment of the ECG extending from a first time to a second time; determining that the first segment includes a shockable rhythm; based on determining that the first segment includes the shockable rhythm, causing the battery to charge the capacitor; identifying a second segment of the ECG extending from a third time to a fourth time; determining whether to discharge the capacitor to the individual by determining whether the second ECG segment includes the shockable rhythm; and outputting a recommendation indicating whether to discharge the capacitor to the individual.

25. The medical device of clause 24, wherein the first time and the second time occur prior to the third time and the fourth time.

26. The medical device of clause 24 or 25, wherein the third time occurs after the first time and prior to the second time.

27. The medical device of any one of clauses 24 to 26, wherein the operations further include: identifying a cardiopulmonary resuscitation (CPR) period, the individual receiving the chest compressions during the CPR period, wherein the first time, the second time, the third time, and the fourth time occur during the CPR period.

28. The medical device of any one of clauses 24 to 27, wherein determining that the first ECG segment includes the shockable rhythm includes: generating a filtered ECG by removing, from the first ECG segment, an artifact corresponding to the chest compressions; generating, based on the filtered ECG, a shock index corresponding to a certainty that the first ECG segment exhibits the shockable rhythm; and comparing the shock index to a threshold.
29. The medical device of any one of clauses 24 to 28, wherein causing the battery to charge the capacitor includes: in response to determining that the first ECG segment includes the shockable rhythm, connecting a battery to the capacitor by closing a switch, wherein the third time occurs when the battery is connected to the capacitor.
30. The medical device of any one of clauses 24 to 29, further including: an output device configured to output the recommendation; an input device configured to receive an input signal; and electrodes connected to the individual; and a discharge circuit configured to discharge energy stored in the capacitor to the electrodes, wherein determining whether to administer the defibrillation shock to the individual by determining whether the second ECG segment includes the shockable rhythm includes: determining that the second ECG segment includes the shockable rhythm; based on determining that the second ECG segment includes the shockable rhythm, causing the output device to output the recommendation; and based on the input signal, administering the defibrillation shock to the individual by causing the discharge circuit to discharge the energy stored in the capacitor to the electrodes.
31. The medical device of any one of clauses 24 to 30, further including: an output device configured to output the recommendation, wherein determining whether to administer a defibrillation shock to the individual by determining whether the second ECG segment includes the shockable rhythm includes: determining that the shockable rhythm is absent from the second ECG segment; and based on determining that the shockable rhythm is absent from the second ECG segment, generate the recommendation to advise against administering the defibrillation shock to the individual.
32. The medical device of any one of clauses 24 to 31, further including: an output device configured to output the recommendation, wherein determining whether to administer a defibrillation shock to the individual by determining whether the second ECG segment includes the shockable rhythm includes: determining that the shockable rhythm is absent from the second ECG segment; and based on determining that the shockable rhythm is absent from the second ECG segment, preventing the discharge circuit from discharging the energy stored in the capacitor to the electrodes.
33. A method performed by a medical device, the method including: identifying a first electrocardiogram (ECG) segment of an individual receiving chest compressions, the first ECG segment extending from a first time to a second time; determining that the first ECG segment includes a shockable rhythm; based on determining that the first ECG segment includes the shockable rhythm, charging a capacitor; identifying a second ECG segment of the individual receiving chest compressions, the second ECG segment extending from a third time to a fourth time; determining whether to discharge the capacitor to the individual by determining whether the second ECG segment includes the shockable rhythm; and outputting a recommendation indicating whether to discharge the capacitor to the individual.
34. The method of clause 33, wherein the first time and the second time occur prior to the third time and the fourth time.
35. The method of clause 33 or 34, wherein the third time occurs after the first time and prior to the second time.
36. The method of any one of clauses 33 to 35, further including: identifying a cardiopulmonary resuscitation (CPR) period, the individual receiving the chest compressions during the CPR period, wherein the first time, the second time, the third time, and the fourth time occur during the CPR period.
37. The method of any one of clauses 33 to 36, wherein determining that the first ECG segment includes the shockable rhythm includes: generating a filtered ECG by removing, from the first ECG segment, an artifact corresponding to the chest compressions; generating, based on the filtered ECG, a shock index corresponding to a certainty that the first ECG segment exhibits the shockable rhythm; and comparing the shock index to a threshold.
38. The method of any one of clauses 33 to 37, wherein charging the capacitor includes: in response to determining that the first ECG segment includes the shockable rhythm, connecting a battery to the capacitor by closing a switch, wherein the third time occurs when the battery is connected to the capacitor.
39. The method of any one of clauses 33 to 38, wherein determining whether to administer a defibrillation shock to the individual by determining whether the second ECG segment includes the shockable rhythm includes: determining that the second ECG segment includes the shockable rhythm; and based on determining that the second ECG segment includes the shockable rhythm, administering the defibrillation shock by discharging energy stored in the capacitor to electrodes connected to the skin of the individual.
40. The method of any one of clauses 33 to 39, wherein determining whether to administer a defibrillation shock to the individual by determining whether the second ECG segment includes the shockable rhythm includes: determining that the second ECG segment includes the shockable rhythm; based on determining that the second ECG segment includes the shockable rhythm, outputting the recommendation advising to administer the defibrillation shock; receiving an input signal associated with the recommendation; and based on the input signal, administering the defibrillation shock to the individual by discharging energy stored in the capacitor to electrodes connected to the skin of the individual.
41. The method of any one of clauses 33 to 40, wherein determining whether to administer a defibrillation shock to the individual by determining whether the second ECG segment includes the shockable rhythm includes: determining that the shockable rhythm is absent from the second ECG segment; and based on determining that the shockable rhythm is absent from the second ECG segment, generating the recommendation to advise against administering the defibrillation shock to the individual.
42. A medical device, including: a detection circuit configured to detect an electrocardiogram (ECG) of an individual; a capacitor; a battery configured to charge the capacitor; a processor; and memory storing instructions that, when executed by the processor, cause the processor to perform operations including: identifying a segment of the ECG extending from a third time to a fourth time; determining that the segment includes the shockable rhythm; based on determining that the segment includes the shockable rhythm, initiating charging of the capacitor by connecting the battery to the capacitor; predicting a charging period of the capacitor based on a charge level of the battery; and outputting an instruction to perform chest compressions on the individual based on the charging period of the capacitor.

43. The medical device of clause 42, further including: a temperature sensor configured to detect a temperature of the medical device, wherein predicting the charging period of the capacitor is based on a capacitance of the capacitor, an internal resistance of the battery, the temperature of the medical device, a dosage level of a defibrillation shock, an impedance of the individual, or a combination thereof.

44. The medical device of clause 42 or 43, wherein the instruction indicates an end time of a cardiopulmonary resuscitation (CPR) period and to perform the chest compressions on the individual during the CPR period, the end time of the CPR period being ten seconds or less after an end time of the charging period.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. An external defibrillator, comprising:
a detection circuit configured to detect an electrocardiogram (ECG) of an individual;
a capacitor;
a battery configured to charge the capacitor;
a discharge circuit configured to discharge the capacitor;
a processor; and memory storing instructions that, when executed by the processor, cause the processor to perform operations comprising:
  identifying an end time of a cardiopulmonary resuscitation (CPR) period, wherein the individual is receiving chest compressions during the CPR period;
  predicting a duration of a charging period of the capacitor based on a charge level of the battery, a capacitance of the capacitor, a temperature of the external defibrillator, and a dosage level of a defibrillation shock;
  determining, based on the end time of the CPR period and the duration of the charging time of the capacitor, a start time of an analysis period;
  identifying a segment of the ECG obtained during the analysis period, the analysis period occurring between the start time and an intermediate time;
  generating a filtered ECG by removing a chest compression artifact from the segment of the ECG;
  determining that the filtered ECG exhibits ventricular fibrillation (VF);
  in response to determining that the filtered ECG exhibits the VF, causing the battery to charge the capacitor during the charging period such that the capacitor is charged at the end time of the CPR period; and
  causing the discharge circuit to discharge energy stored in the capacitor to the individual as the defibrillation shock at the end of the CPR period.

2. The external defibrillator of claim 1, further comprising:
  a display configured to visually output a recommendation;
  an input device configured to receive an input signal from a user,
  wherein the operations further comprise:
  generating the recommendation based on determining that the filtered ECG exhibits the shockable rhythm, and
  wherein causing the discharge circuit to discharge the energy stored in the capacitor to the individual is in response to the input device receiving the input signal.

3. The external defibrillator of claim 1, wherein a time period between the start time of the analysis period and the end time of the CPR period is greater than or equal to a sum of the charging period and the analysis period.

4. A medical device, comprising:
  a detection circuit configured to detect an electrocardiogram (ECG) of an individual;
  a capacitor;
  a battery configured to charge the capacitor;
  a processor; and
  memory storing instructions that, when executed by the processor, cause the processor to perform operations comprising:
    identifying an end time of a cardiopulmonary resuscitation (CPR) period, the individual receiving chest compressions during the CPR period;
    determining a length of a charging period of the capacitor based on a charge level of the battery;
    determining, based on the length of the charging period of the capacitor, a start time of an analysis period;
    identifying, during the analysis period and the CPR period, a segment of the ECG;
    determining that the segment of the ECG comprises a shockable rhythm; and
    in response to determining that the segment of the ECG comprises the shockable rhythm, causing the battery to charge the capacitor such that the capacitor is charged at the end time of the CPR period.

5. The medical device of claim 4, further comprising:
  a temperature sensor configured to detect a temperature of the medical device,
  wherein determining the length of the charging period of the capacitor is based on a capacitance of the capacitor, an internal resistance of the battery, the temperature of the medical device, a dosage level of a defibrillation shock, an impedance of the individual, or a combination thereof.

6. The medical device of claim 4, wherein the operations further comprise:
  predicting a length of the analysis period,
  wherein determining the start time of the analysis period is further based on the length of the analysis period.

7. The medical device of claim 4, wherein determining that the segment of the ECG comprises the shockable rhythm comprises:
  generating a filtered ECG by removing a chest compression artifact from the segment of the ECG;
  generating a shock index based on the filtered ECG; and
  comparing the shock index to a threshold.

8. The medical device of claim 4, wherein the capacitor is charged within ten seconds before the end time of the CPR period.

9. The medical device of claim 4, wherein a time period between the start time of the analysis period and the end time of the CPR period is greater than or equal to a sum of the length of the charging period and a length of the analysis period.

10. The medical device of claim 4, further comprising:
  a discharge circuit configured to discharge the capacitor; and
  electrodes connected to the skin of the individual,
  wherein the operations further comprise:
    causing the discharge circuit to discharge energy stored in the charged capacitor to the electrodes.

11. The medical device of claim 10, further comprising:
  an output device configured to output a recommendation to administer a defibrillation shock; and
  an input device configured to receive an input signal,
  wherein the operations further comprise:
    determining that the capacitor is charged;
    based on determining that the capacitor is charged, causing the output device to output the recommendation to administer the defibrillation shock; and
    receiving an input signal based on the recommendation, and
  wherein causing the discharge circuit to discharge the energy stored in the charged capacitor to the electrodes is in response to receiving the input signal.

12. The medical device of claim 10, wherein the discharge circuit comprises first switches, and
  wherein causing the discharge circuit to discharge the energy stored in the charged capacitor to the electrodes comprises:
    disconnecting the battery from the capacitor by opening a second switch; and
    connecting the capacitor to the electrodes by closing the first switches in the discharge circuit.

13. A method performed by a medical device, the method comprising:
  identifying an end time of a cardiopulmonary resuscitation (CPR) period, wherein an individual is receiving chest compressions during the CPR period;
  determining, based on a charge level of a battery, a length of a charging period of a capacitor of the medical device;

determining, based on the end time of the CPR period and the length of the charging period of the capacitor, a start time of an analysis period that overlaps the CPR period;

identifying, during the analysis period, a segment of an electrocardiogram (ECG) of the individual;

determining that the segment of the ECG comprises a shockable rhythm; and based on determining that the segment of the ECG comprises the shockable rhythm, charging the capacitor during the charging period by connecting the battery to the capacitor, the capacitor being charged at the end time of the CPR period.

14. The method of claim 13, wherein determining the charging period of the capacitor comprises determining a capacitance of the capacitor, determining an internal resistance of the battery, determining a temperature of the medical device, determining a dosage level of a defibrillation shock, determining an impedance of the individual, or a combination thereof.

15. The method of claim 13, further comprising:
determining a length of the analysis period,
wherein determining the start time of the analysis period is further based on the length of the analysis period.

16. The method of claim 13, wherein determining that the segment of the ECG comprises the shockable rhythm comprises:

generating a filtered ECG by removing a chest compression artifact from the segment of the ECG;

generating a shock index based on the filtered ECG; and comparing the shock index to a threshold.

17. The method of claim 13, wherein the capacitor is charged within ten seconds before the end time of the CPR period.

18. The method of claim 13, wherein a time period between the start time of the analysis period and the end time of the CPR period is greater than or equal to a sum of the length of the charging period and a length of the analysis period.

19. The method of claim 13, further comprising:
administering a defibrillation shock to the individual by discharging the charged capacitor.

20. The method of claim 19, further comprising:
outputting a recommendation to administer the defibrillation shock; and
receiving an input signal based on the recommendation,
wherein administering the defibrillation shock to the individual by discharging the capacitor is in response to receiving the input signal.

* * * * *